(12) United States Patent
Lopez et al.

(10) Patent No.: US 9,193,699 B2
(45) Date of Patent: Nov. 24, 2015

(54) APOPTOSIS INDUCING COMPOUNDS

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE (C.N.R.S), Paris (FR); UNIVERSITE D'AIX-MARSEILLE, Marseilles (FR); L'INSTITUT PAOLI CALMETTE, Marseilles (FR)

(72) Inventors: Marc Lopez, Marseill (FR); Yves Collette, Marseilles (FR); Lynda Mezil, Marseilles (FR); Jean-Michel Brunel, Marseilles (FR); Sebastien Combes, Marseilles (FR)

(73) Assignees: INSTITUT NATIONAL DE LA SANTE ET DE LA RECHERCHE MEDICALE (INSERM, Paris (FR); CENTRE NATIONAL DE LA RECHERCHE SCIENTIFIQUE (C.N.R.S.), Paris (FR); UNIVERSITÉ D'AIX-MARSEILLE, Marseilles (FR); L'INSTITUT PAOLI-CALMETTES, Marseilles (FR)

( * ) Notice: Subject to any disclaimer, the term of this patent is extended or adjusted under 35 U.S.C. 154(b) by 0 days.

(21) Appl. No.: 14/349,529

(22) PCT Filed: Oct. 4, 2012

(86) PCT No.: PCT/EP2012/069629
§ 371 (c)(1),
(2) Date: Apr. 3, 2014

(87) PCT Pub. No.: WO2013/050476
PCT Pub. Date: Apr. 11, 2013

(65) Prior Publication Data
US 2014/0296227 A1    Oct. 2, 2014

(30) Foreign Application Priority Data
Oct. 4, 2011    (EP) .................................... 11306286

(51) Int. Cl.
*C07D 279/12*    (2006.01)

(52) U.S. Cl.
CPC .................... *C07D 279/12* (2013.01)

(58) Field of Classification Search
CPC ...................................................... C07D 279/12
USPC .......................................... 544/59; 514/227.5
See application file for complete search history.

(56) References Cited

U.S. PATENT DOCUMENTS
2003/0096737 A1    5/2003    Diu-Hercend et al.

FOREIGN PATENT DOCUMENTS
WO        98/34918 A1    8/1998
WO        99/58531 A1    11/1999

OTHER PUBLICATIONS

Polunovsky et al., "Induction of Endothelial Cell Apoptosis by TNFalpha: Modulation by Inhibitors of Protein Synthesis", Experimental Cell Research, Oct. 1, 1994, pp. 584-594, vol. 214, No. 2, Academic Press, US.

*Primary Examiner* — Kahsay Habte
(74) *Attorney, Agent, or Firm* — Whitham, Curtis, Christofferson & Cook, P.C.

(57) ABSTRACT

Provided are compounds of formula (I):

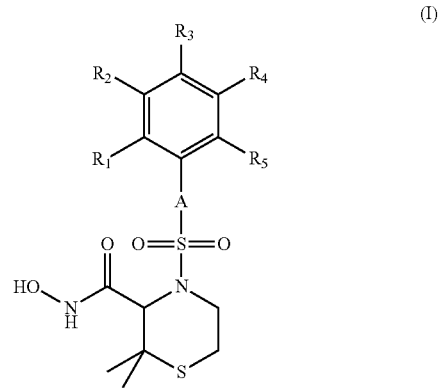

wherein $R_1$, $R_2$, $R_3$, $R_4$ and $R_5$ are independently selected from the group comprising, inter aliae, H, optionally substituted, branched or linear $C_1$-$C_{12}$ alkyl, halogen atom and $C_1$-$C_{12}$ haloalkyl, and wherein A represents a single bond or an optionally substituted $C_1$-$C_6$ alkylene radical, notably useful for the treatment of human cancers.

17 Claims, 7 Drawing Sheets

APOPTOSIS INDUCING COMPOUNDS

CROSS-REFERENCE TO RELATED APPLICATIONS

This application is a Rule 371 application of International Application PCT/EP2012/069629 filed Oct. 4, 2012.

The present invention relates to sulfonylthiomorpholine-3-carboxamide compounds, their methods of preparation, as well as uses thereof for the treatment of human neoplasms.

Treatment of cancer with radiotherapy and/or anticancer drug is frequently associated with increased apoptosis mechanisms. However, resistance to treatments is a common feature in cancer therapy. This may be related to a reduced ability to cancer cells to undergo apoptosis.

Apoptosis is a fine-tuned biological process. In the case of cancer cells, the apoptotic balance is in favour of cell survival. Resistance to apoptosis is mainly due to quantitative (expression) and/or qualitative (mutations) alterations in proteins involved in the apoptotic cascade. To reach full range apoptosis, different non exclusive signalling pathways are implicated. These pathways are regulated by different actors, but share common end points, i.e. the activation of procaspase-3 and procaspase-7 into caspase-3 and caspase-7 respectively, that are effector caspases. Once activated, these caspases cleave other substrates that trigger apoptosis processes.

Different approaches have been tested to induce cancer cell apoptosis. These approaches generally used small molecules.

However, since normal cells are also sensitive to apoptosis, these small molecules may present the inconvenient to kill also normal cells. This point represents a major caveat regarding the use of such molecules in clinics.

Thus, the development of new compounds capable of inducing tumor apoptosis with reduced effect on normal cells is of outstanding interest in the field of tumor treatment.

In prior art, several compounds with a sulfonylthiomorpholine-3-carboxamide structure have been studied, notably for their anticancer activity.

For example, US 2002/0156074, WO 2010/007027 and WO 98/34918 describe compounds useful for the treatment of diseases mediated by a matrix metalloproteinase (MMP) enzyme. Almstead et al. (J. Med. Chem. 1999, Vol. 42, no 22, 4547-4562) describes thiazine- and thiazepine-based MMP inhibitors. Several other documents of prior art describe compounds TMI-1 and apratastat, known as TACE/MMP inhibitors, exhibiting a sulfonylthiomorpholine-3-carboxamide structure.

However, none of those previously described compounds have been shown to exhibit an apoptosis inducing activity.

One of the aims of the present invention is to provide new apoptosis inducing compounds having a strong apoptosis inducing activity towards tumor cells at nanomolar range.

Another aim of the present invention is to provide new apoptosis inducing compounds having a reduced cytotoxicity, or even no cytotoxicity, towards normal cells.

Another aim of the present invention is to provide compounds able to activate procaspase-3 and procaspase-7.

The present invention relates to a compound of formula (I):

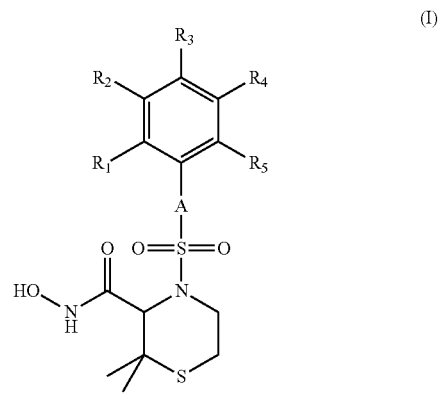

wherein $R_1$, $R_2$, $R_4$ and $R_5$ are independently selected from the group consisting of:
H,
optionally substituted, branched or linear $C_1$-$C_{12}$ alkyl,
optionally substituted, branched or linear $C_2$-$C_{12}$ alkenyl,
halogen atom,
$C_1$-$C_{12}$ haloalkyl,
$(CH_2)_a R^a$ wherein a is comprised from 1 to 12 and $R^a$ is selected from the group consisting of:
  $OR^{a1}$, wherein $R^{a1}$ is selected from the group consisting of optionally substituted $C_1$-$C_{12}$ alkyl, optionally substituted $C_6$-$C_{10}$ aryl, optionally substituted $C_3$-$C_{12}$ cycloalkyl, optionally substituted $C_2$-$C_6$ heterocycloalkyl and optionally substituted $C_1$-$C_{10}$ heteroaryl, and
  $R^{a2}$ wherein $R^{a2}$ is selected from the group consisting of optionally substituted $C_6$-$C_{10}$ aryl, optionally substituted $C_3$-$C_{12}$ cycloalkyl, optionally substituted $C_2$-$C_6$ heterocycloalkyl and optionally substituted $C_1$-$C_{10}$ heteroaryl,
$(CH_2)_b R^b$ wherein b is comprised from 0 to 12 and $R^b$ is selected from the group consisting of:
  CN,
  OH,
  $C(O)R^{b1}$ and $SO_2 R^{b1}$, wherein $R^{b1}$ is selected from the group consisting of H, OH, optionally substituted $C_1$-$C_{12}$ alkyl, optionally substituted $C_6$-$C_{10}$ aryl, optionally substituted $C_3$-$C_{12}$ cycloalkyl, optionally substituted $C_2$-$C_6$ heterocycloalkyl and optionally substituted $C_1$-$C_{10}$ heteroaryl, and
  $NHR^{b2}$ and $NHC(O)R^{b2}$ wherein $R^{b2}$ is selected from the group consisting of H, optionally substituted $C_1$-$C_{12}$ alkyl,
wherein $R_3$ is selected from the group consisting of:
H,
optionally substituted, branched or linear $C_1$-$C_{12}$ alkyl,
optionally substituted, branched or linear $C_2$-$C_{12}$ alkenyl,
halogen atom,
$C_1$-$C_{12}$ haloalkyl,
$(CH_2)_a R^a$ wherein a is comprised from 1 to 12 and $R^a$ is selected from the group consisting of:
  $OR^{a1}$, wherein $R^{a1}$ is selected from the group consisting of optionally substituted $C_1$-$C_{12}$ alkyl, optionally substituted $C_3$-$C_{12}$ cycloalkyl, and optionally substituted $C_2$-$C_6$ heterocycloalkyl, and $R^{a2}$ wherein $R^{a2}$ is selected from the group consisting of optionally substituted $C_6$-$C_{10}$ aryl, optionally substituted $C_3$-$C_{12}$ cycloalkyl, optionally substituted $C_2$-$C_6$ heterocycloalkyl and optionally substituted $C_1$-$C_{10}$ heteroaryl, $(CH_2)_b R^b$ wherein b and $R^b$ are as defined above, and wherein A represents a single bond or a $C_1$-$C_6$ alkylene radical, optionally substituted by a $C_1$-$C_6$ alkyl or a $C_6$-$C_{10}$ aryl group.

According to the invention, $R_3$ is not a group of formula O-alkyl-aryl.

According to the invention, $R_3$ is not a group of formula O-alkyl-heteroaryl.

According to one embodiment, a is comprised from 1 to 10, more specifically from 1 to 6, advantageously from 1 to 3.

According to another embodiment, a is 1 or 2.

According to another embodiment, b is comprised from 0 to 10, more specifically from 0 to 6, advantageously from 0 to 3.

According to another embodiment, b is 0.

According to another embodiment, b is 1 or 2.

According to one embodiment, in formula (I), $R_3$=H.

According to another embodiment, in formula (I), $R_3$ is different from H.

According to one embodiment, in formula (I), $R_3$ is selected from the group consisting of:

H, optionally substituted, branched or linear $C_1$-$C_{12}$ alkyl, optionally substituted, branched or linear $C_2$-$C_{12}$ alkenyl, halogen atom, $C_1$-$C_{12}$ haloalkyl, $(CH_2)_a R^a$ wherein a is comprised from 1 to 12 and $R^a$ is selected from the group consisting of optionally substituted $C_6$-$C_{10}$ aryl, optionally substituted $C_3$-$C_{12}$ cycloalkyl, optionally substituted $C_2$-$C_6$ heterocycloalkyl and optionally substituted $C_1$-$C_{10}$ heteroaryl, and $(CH_2)_b R^b$ wherein b and $R^b$ are as defined above.

According to one embodiment, in formula (I), $R_3$ is selected from the group consisting of:

H, optionally substituted, branched or linear $C_1$-$C_{12}$ alkyl, optionally substituted, branched or linear $C_2$-$C_{12}$ alkenyl, halogen atom, $C_1$-$C_{12}$ haloalkyl, $(CH_2)_a R^a$ wherein a is comprised from 1 to 12 and $R^a$ is selected from the group consisting of optionally substituted $C_3$-$C_{12}$ cycloalkyl, and optionally substituted $C_2$-$C_6$ heterocycloalkyl, and $(CH_2)_b R^b$ wherein b and $R^b$ are as defined above.

According to one embodiment, in formula (I), $R_3$ is selected from the group consisting of H, optionally substituted, branched or linear $C_1$-$C_{12}$ alkyl, halogen atom and $C_1$-$C_{12}$ haloalkyl.

According to one embodiment, in formula (I), $R_3$ is an optionally substituted, branched or linear $C_1$-$C_{12}$ alkyl, more specifically comprising from 1 to 6, advantageously from 1 to 3 carbon atoms.

According to another embodiment, in formula (I), $R_3$ is a $C_1$-$C_{12}$ haloalkyl, more specifically comprising from 1 to 6, advantageously from 1 to 3 carbon atoms.

According to another embodiment, in formula (I), $R_3$ is an halogen atom, for example a fluorine atom.

According to one embodiment, in formula (I), $R_1$, $R_2$, $R_4$ and $R_5$ are independently selected from the group consisting of H and optionally substituted, branched or linear $C_1$-$C_{12}$ alkyl.

According to one embodiment, in formula (I), $R_1$, $R_2$, $R_4$ and $R_5$ are independently selected from the group consisting of H and methyl.

According to one embodiment, in formula (I), $R_1$, $R_2$, $R_4$ and $R_5$ are methyl.

According to another embodiment, in formula (I), $R_1$, $R_3$ and $R_5$ are independently selected from the group consisting of H and optionally substituted, branched or linear $C_1$-$C_{12}$ alkyl.

According to one embodiment, in formula (I), $R_1$, $R_3$ and $R_5$ are independently selected from the group consisting of H, methyl and isopropyl.

According to one embodiment, in formula (I), $R_1$=$R_5$.

According to one embodiment, in formula (I), $R_2$=$R_4$.

According to one embodiment, in formula (I), $R_1$=$R_3$=$R_5$.

According to one embodiment, in formula (I), A represents a single bond or a $C_2$ alkylene radical substituted by a phenyl group.

The compounds of formula (I) according to the invention present a strong apoptosis inducing activity towards tumor cells, and promote the activation of procaspase-3 and procaspase-7.

In the present invention, the terms "activation of procaspase" refer to the cleavage of inactive procaspase to provide the active caspase, that then triggers apoptosis processes.

Furthermore, the compounds of formula (I) according to the invention present the advantage of having a reduced cytotoxicity, or even no cytotoxicity, towards normal cells. The compounds according to the invention are thus suitable for the treatment of cancers, particularly those exhibiting a resistance to drug treatments.

According to the invention, the term "alkyl" designates a saturated hydrocarbonated group, linear or branched, having more particularly from 1 to 12, preferably from 1 to 10, more specifically from 1 to 4 carbon atoms, such as methyl, ethyl, propyl, isopropyl, n-butyl, isobutyl, tert-butyl, pentyl, neopentyl, n-hexyl, heptyl, octyl, nonyl, decyl, dodecyl, undecyl, dodecyl.

According to the invention, the term "alkenyl" designates a partially unsaturated, nonaromatic, hydrocarbon groups having 2 to 12, preferably 2 to 6 carbon atoms, more specifically from 2 to 4 carbon atoms, such as vinyl, allyl, propenyl, isopropenyl, crotyl, butenyl.

According to the invention, the term "cycloalkyl" designates saturated cyclic, bicyclic, tricyclic, or polycyclic hydrocarbon groups having 3 to 12, preferably 5 to 10 carbon atoms, wherein any ring atom capable of substitution may be substituted by a substituent. Examples of cycloalkyl moieties include, but are not limited to, cyclohexyl and adamantyl.

According to the invention, the term "halo" refers to the atoms of the group 17 of the periodic table (halogens) and includes in particular fluorine, chlorine, bromine, and iodine atom.

According to the invention, the term "haloalkyl" refers to an alkyl group in $C_1$-$C_{12}$ wherein at least one atom of hydrogen has been replaced by a halogen atom, such as bromomethyl, fluoromethyl, iodomethyl, chloromethyl, trifluoromethyl; and to alkyl group in $C_1$-$C_{12}$ wherein all the atoms of hydrogen have been replaced by a halogen atom, such as perfluoroalkyl groups.

According to the invention, the term "aryl" refers to an aromatic monocyclic, bicyclic, or tricyclic hydrocarbon ring system, having 6 to 10, preferably 6 carbon atoms, wherein any ring atom capable of substitution may be substituted by a substituent. Examples of aryl moieties include, but are not limited to, phenyl and naphthyl.

According to the invention, the term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g. carbon atoms and 1-3, 1-6, or 1-9 heteroatoms of N, O, or S if monocyclic, bicyclic, or tricyclic, respectively), wherein any ring atom capable of substitution may be substituted by a substituent.

According to the invention, the term "heterocycloalkyl" refers to a nonaromatic 5-7 membered monocyclic, ring system having 1-3 heteroatoms, said heteroatoms being selected from O, N, or S (e.g. carbon atoms and 1-3 heteroatoms of N, O, or S), wherein any ring atom capable of substitution may be substituted by a substituent.

According to the invention, the term "substituents" refers to a group "substituted" on an alkyl, heterocycloalkyl, aryl or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$ alkyl (where n is 0-2), $S(O)_n$ aryl (where n is 0-2), $S(O)_n$ heteroaryl (where n is 0-2), $S(O)_n$ heterocycloalkyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocycloalkyl, and unsubstituted cycloalkyl.

According to the invention, the term "acyl" refers to an alkylcarbonyl, cycloalkylcarbonyl, arylcarbonyl, heterocycloalkylcarbonyl, or heteroarylcarbonyl substituent, any of which may be further substituted by substituents.

The compounds herein described may have asymmetric centers. Compounds of the present invention containing an asymmetrically substituted atom may be isolated in optically active or racemic forms. It is well-known in the art how to prepare optically active forms, such as by resolution of racemic forms or by synthesis from optically active starting materials. All chiral, diastereomeric, racemic forms and all geometric isomeric forms of a compound are intended, unless the stereochemistry or the isomeric form is specifically indicated.

The compounds of the invention also encompass their stereoisomers (diastereoisomers, enantiomers), pure or mixed, racemic mixtures, geometrical isomers, tautomers, salts, hydrates, solvates, solid forms as well as their mixtures.

This invention concerns "pharmaceutically acceptable" salts of compounds according to the invention. Generally, this term designates slightly- or non-toxic salts obtained from organic or inorganic bases or acids. These salts may be obtained during the final purification step of the compound according to the invention or by incorporating the salt into the purified compound.

Some compounds according to the invention and their salts could be stable in several solid forms. The present invention includes all the solid forms of the compounds according to the invention which includes amorphous, polymorphous, mono- and polycrystalline forms. The compounds according to the invention can exist in non-solvated or solvated form, for example with pharmaceutically acceptable solvents such as water (hydrates) or ethanol.

"Pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable salt" refers to salts which retain the biological effectiveness and properties of the compounds of the invention and which are not biologically or otherwise undesirable. In many cases, the compounds of the invention are capable of forming acid and/or base salts by virtue of the presence of amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts see Berge et al. ((1977) J. Pharm. Sd, vol. 66, 1). The expression "non-toxic pharmaceutically acceptable salts" refers to non-toxic salts formed with nontoxic, pharmaceutically acceptable inorganic or organic acids or inorganic or organic bases. For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, and toluenesulfonic acid and the like.

In the context of the invention, the term "treating" or "treatment", as used herein, means reversing, alleviating, inhibiting the progress of, or preventing the disorder or condition to which such term applies, or one or more symptoms of such disorder or condition.

According to one embodiment, in formula (I), $R_1$, $R_2$, $R_3$, $R_4$ and $R_5$ are independently selected from the group consisting of:

H optionally substituted, branched or linear $C_1$-$C_{12}$ alkyl, halogen atom, and $C_1$-$C_{12}$ haloalkyl.

As alkyl group, one may cite $C_1$-$C_6$, advantageously $C_1$-$C_4$ alkyl groups.

As alkyl group, one may cite methyl, ethyl, propyl, isopropyl and dodecyl, advantageously methyl and isopropyl.

As halogen atom, one may cite fluorine atom.

As haloalkyl group, one may cite bromomethyl and trifluoroalkyl.

According to a first embodiment of the present invention, A represents a single bond.

The compounds of formula (I) according to this embodiment are phenylsulfonylthiomorpholine-3-carboxamide compounds.

The present invention also relates to a compound of formula (II):

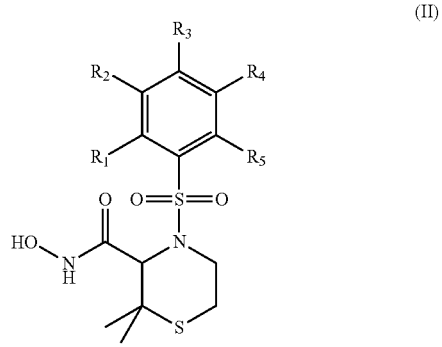

wherein $R_1$, $R_2$, $R_3$, $R_4$ and $R_5$ are as defined above in formula (I).

According to one embodiment, in formula (II), $R_1$, $R_2$, $R_3$, $R_4$ and $R_5$ are independently selected from the group consisting of:

H optionally substituted, branched or linear $C_1$-$C_{12}$ alkyl, $C_1$-$C_{12}$ haloalkyl.

As alkyl group, one may cite $C_1$-$C_6$, advantageously $C_1$-$C_4$ alkyl groups.

As alkyl group, one may cite methyl, ethyl, propyl, isopropyl and dodecyl, advantageously methyl and isopropyl.

As halogen atom, one may cite fluorine atom.

As haloalkyl group, one may cite bromomethyl and trifluoroalkyl.

According to one embodiment, in formula (I) or (II), $R_1$, $R_2$, $R_4$ and $R_5$ are H.

According to one embodiment, the compounds of formula (II) have the following formula (II-1):

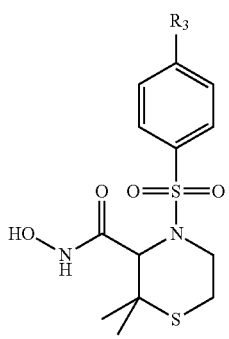

(II-1)

wherein $R_3$ is as defined above in formula (I).

According to one embodiment, in formula (II) or (II-1), $R_3$ is H.

According to another embodiment, in formula (II) or (II-1), $R_3$ is other than H.

According to one embodiment, in formula (II) or (II-1), $R_3$ is selected from the group consisting of H, optionally substituted, branched or linear $C_1$-$C_{12}$ alkyl, halogen atom and $C_1$-$C_{12}$ haloalkyl.

According to one embodiment, in formula (II) or (II-1), $R_3$ is an optionally substituted, branched or linear $C_1$-$C_{12}$ alkyl, more specifically comprising from 1 to 6, advantageously from 1 to 3 carbon atoms.

According to one embodiment, in formula (II) or (II-1), $R_3$ is a $C_1$-$C_{12}$ haloalkyl, more specifically comprising from 1 to 6, advantageously from 1 to 3 carbon atoms.

According to one embodiment, in formula (II) or (II-1), $R_3$ is an halogen atom, for example a fluorine atom.

According to one embodiment, in formula (II) or (II-1), $R_3$ is selected from the group consisting of H, methyl, ethyl, propyl, isopropyl, dodecyl, bromomethyl, trifluoromethyl and fluor.

According to one embodiment, in formula (II) or (II-1), $R_3$ is isopropyl.

As compounds according to formula (II-1), one may cite the following compounds:

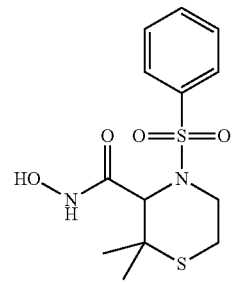

1

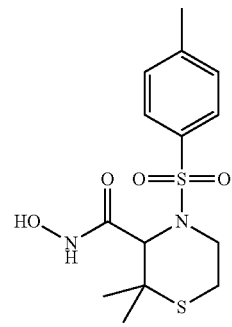

2

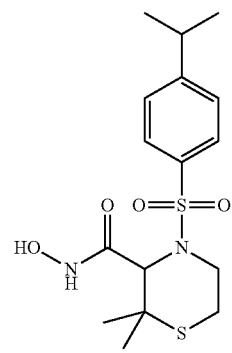

3

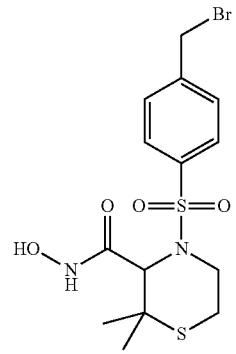

5

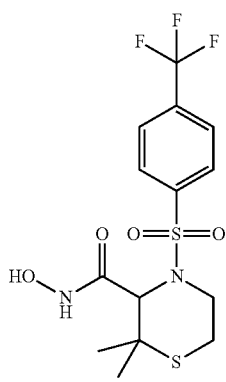

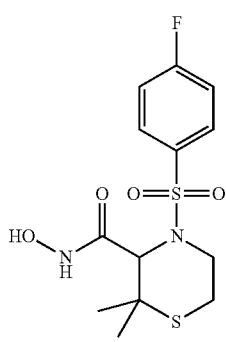

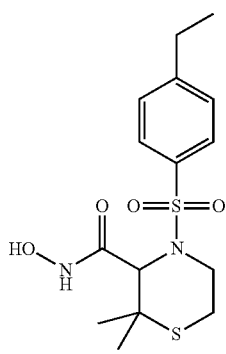

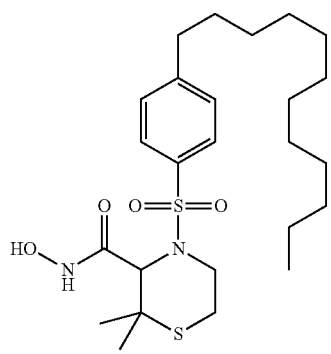

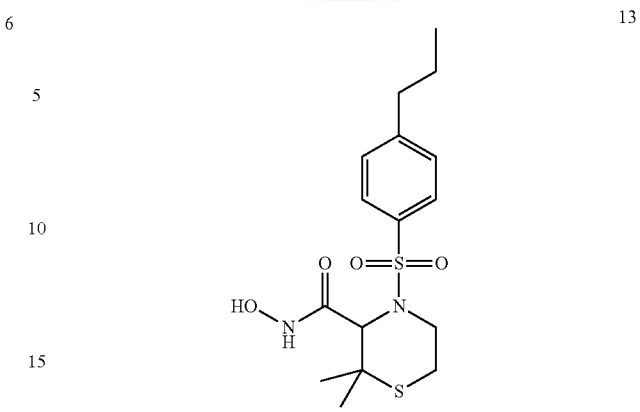

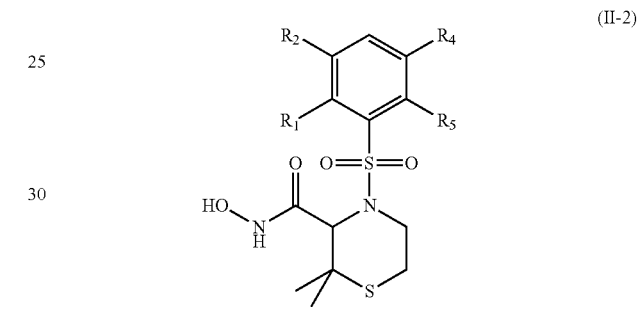

According to one embodiment, in formula (I) or (II), R₃ is H.

According to one embodiment, the compounds of formula (II) have the following formula (II-2):

$$\text{(II-2)}$$

wherein $R_1$, $R_2$, $R_4$ and $R_5$ are as defined above in formula (I).

According to one embodiment, in formula (II) or (II-2), $R_2 = R_4$.

According to one embodiment, in formula (II) or (II-2), $R_1 = R_3$.

According to one embodiment, in formula (II) or (II-2), $R_1$, $R_2$, $R_4$ and $R_5$ are independently selected from the group consisting of H and optionally substituted, branched or linear $C_1$-$C_{12}$ alkyl.

According to one embodiment, in formula (II) or (II-2), $R_1$, $R_2$, $R_4$ and $R_5$ are independently selected from the group consisting of H and methyl.

According to one embodiment, in formula (II) or (II-2), $R_1$, $R_2$, $R_4$ and $R_5$ are methyl.

As compounds according to formula (II-2), one may cite the following compounds:

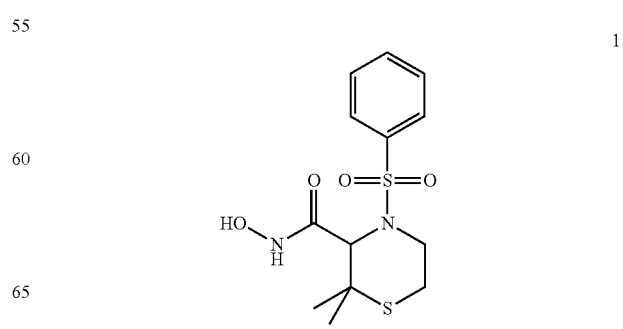

-continued

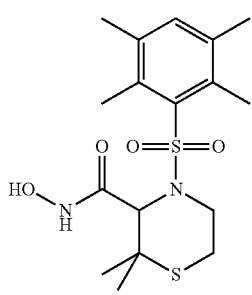

4

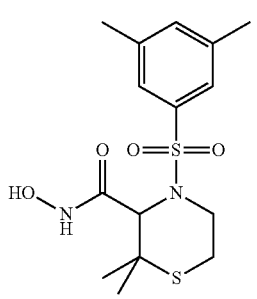

14

According to one embodiment, in formula (I) or (II), $R_2$ and $R_4$ are H.

As compounds of formula (II), one may cite the compounds having the following formula (II-3):

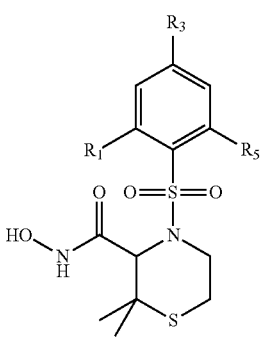

(II-3)

wherein $R_1$, $R_3$ and $R_5$ are as defined above in formula (I).

According to one embodiment, in formula (II) or (II-3), $R_1=R_5$.

According to one embodiment, in formula (II) or (II-3), $R_1=R_3=R_5$.

According to one embodiment, in formula (II) or (II-3), $R_1$, $R_3$ and $R_5$ are independently selected from the group consisting of H and optionally substituted, branched or linear $C_1$-$C_{12}$ alkyl.

According to one embodiment, in formula (II) or (II-3), $R_1$, $R_3$ and $R_5$ are independently selected from the group consisting of optionally substituted, branched or linear $C_1$-$C_{12}$ alkyl.

According to one embodiment, in formula (II) or (II-3), $R_1$, $R_3$ and $R_5$ are independently selected from the group consisting of H, methyl and isopropyl.

As compounds according to formula (II-3), one may cite the following compounds:

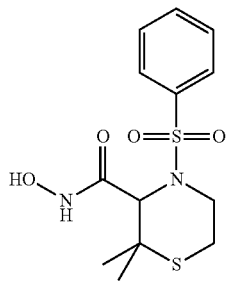 [SMILES: CC1(C)SCCN(S(=O)(=O)c2ccccc2)C1C(=O)NO]

1

11

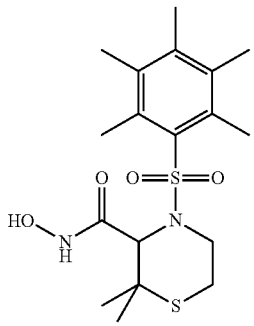

According to another embodiment of the present invention, in formula (I), none of $R_1$, $R_2$, $R_3$, $R_4$ and $R_5$ is H.

According to one embodiment, $R_1=R_2=R_3=R_4=R_5$.

According to one embodiment, $R_1$, $R_2$, $R_3$, $R_4$ and $R_5$ are chosen from optionally substituted, branched or linear $C_1$-$C_{12}$ alkyl, such as methyl.

As compound according to this embodiment, one may cite the following compound:

12

According to another embodiment of the present invention, in formula (I), A represents a substituted $C_1$-$C_6$ alkylene radical.

According to one embodiment, A is an ethylene radical substituted by an aryl group, such as a phenyl group.

As compound according to this embodiment, one may cite the following compound:

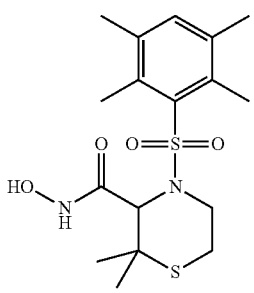
9
According to one embodiment, in formula (I), the two groups positioned in ortho position in respect to radical A are identical, i.e. $R_1=R_5$.
According to one embodiment, in formula (I), the two groups positioned in meta position in respect to radical A are identical, i.e. $R_2=R_4$.
The present invention also relates to the following compounds:
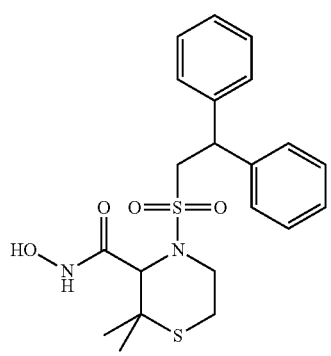
1
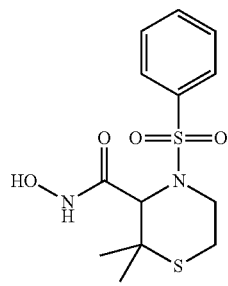
2
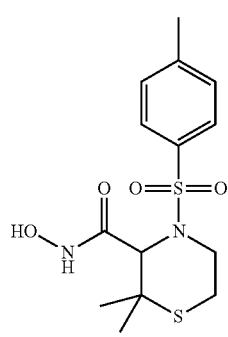
3
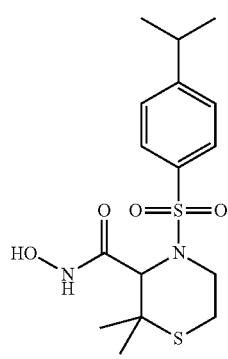
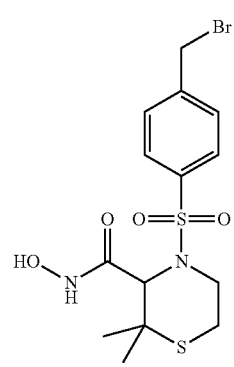
4
5
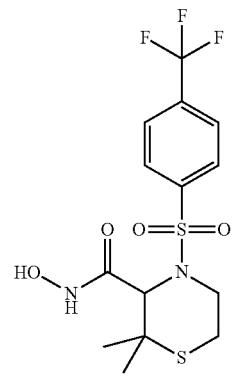
6
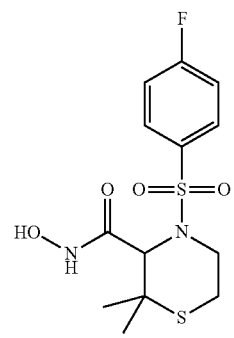
7

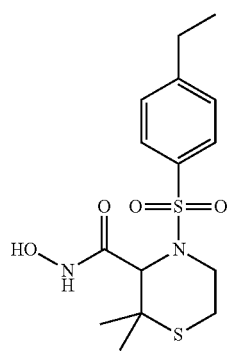

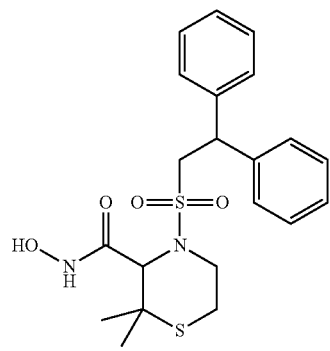

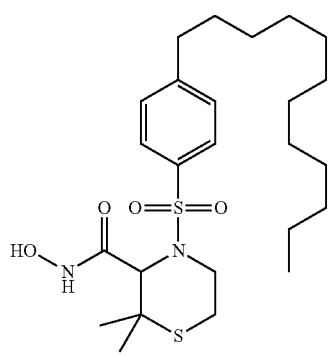

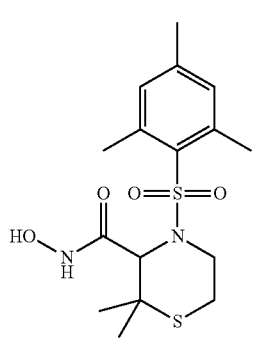

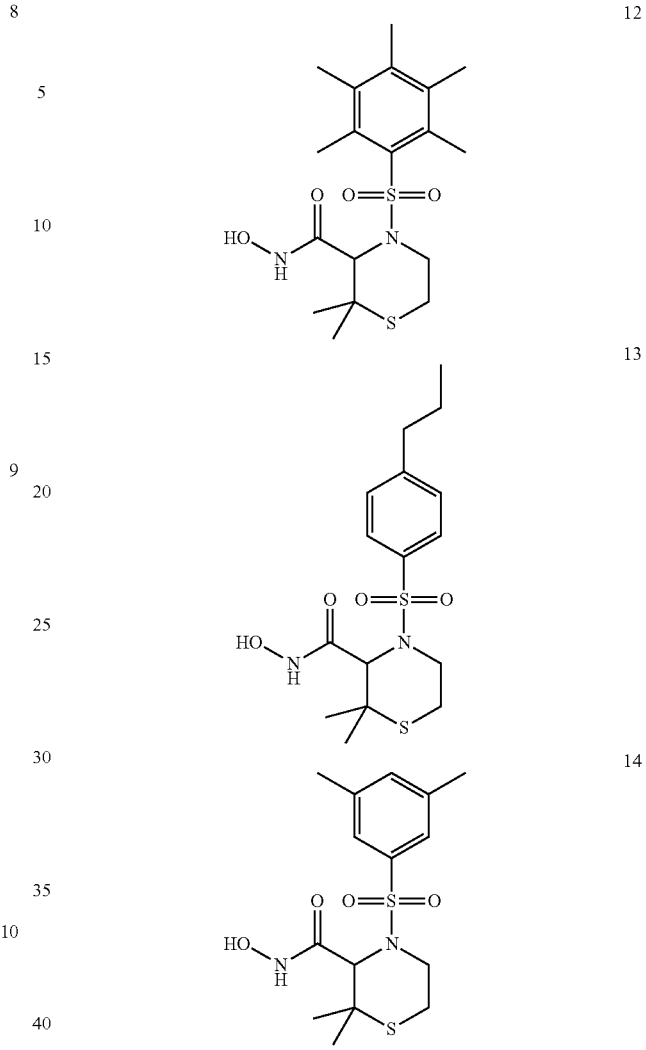

The present invention also relates to a medicament comprising a compound of formula (I) as defined above.

The present invention also relates to a medicament comprising a compound of formula (II), (II-1), (II-2) or (II-3) as described above.

The present invention also relates to a medicament comprising any compound as above described.

The present invention also relates to a compound of formula (I) as above described, for its use as a drug.

The present invention also relates to a compound of formula (II), (II-1), (II-2) or (II-3) as described above for its use as a drug.

The present invention also relates to a compound as described above for its use as a drug.

The present invention also relates to a pharmaceutical composition comprising a compound of formula (I) as defined above, in admixture with one or more pharmaceutically acceptable excipients.

The present invention also relates to a pharmaceutical composition comprising a compound of formula (II), (II-1), (II-2) or (II-3) as defined above, in admixture with one or more pharmaceutically acceptable excipients.

The present invention also relates to a pharmaceutical composition comprising any one of the compounds described above, in association with at least one pharmaceutically acceptable excipient.

The present invention also relates to a compound of formula (I), (II), (II-1), (II-2) or (II-3), or any compound as above described, for its use as apoptosis inducing compound.

The present invention also relates to a compound of formula (I), (II), (II-1), (II-2) or (II-3), or any compound as above described, for its use as procaspase-3 and/or procaspase-7 activator.

According to one embodiment, said compounds of formula (I) are administered together with an antitumoral medicine.

According to one embodiment, said compounds of formula (I) are administered prior, during or after a radiotherapy treatment sequence.

The present invention also relates to a combination comprising a compound of formula (I) as defined above and an antitumoral medicine.

The present invention also relates to a combination of a compound of formula (I) with an antitumoral drug for its use as a drug.

While it is possible for the compounds of the invention having formula (I) to be administered alone it is preferred to present them as pharmaceutical compositions. The pharmaceutical compositions, both for veterinary and for human use, useful according to the present invention comprise at least one compound having formula (I) as above defined, together with one or more pharmaceutically acceptable carriers and optionally other therapeutic ingredients.

In certain embodiments, active ingredients necessary in combination therapy may be combined in a single pharmaceutical composition for simultaneous administration.

As used herein, the term "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The pharmaceutical compositions can be administered in a suitable formulation to humans and animals by topical or systemic administration, including oral, rectal, nasal, buccal, ocular, sublingual, transdermal, rectal, topical, vaginal, parenteral (including subcutaneous, intra-arterial, intramuscular, intravenous, intradermal, intrathecal and epidural), intracisternal and intraperitoneal. It will be appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Total daily dose of the compounds of the invention administered to a subject in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The present invention also relates to a compound of formula (I) as above described, for its use for the treatment and/or the prevention of human neoplasms, such as benign neoplasm, carcinoma and cancer.

The present invention also relates to a compound of formula (II), (II-1), (II-2) or (II-3) or any compound as above described, for its use for the treatment and/or the prevention of human neoplasms, such as benign neoplasm, carcinoma and cancer.

The present invention also relates to a compound of formula (I) as above described, for its use for the inhibition of abnormal proliferation of cells.

The present invention also relates to a compound of formula (II), (II-1), (II-2) or (II-3) or any compound as above described, for its use for the inhibition of abnormal proliferation of cells.

According to one embodiment, the compounds of formula (I), (II), (II-1), (II-2) or (II-3), or any compound as described above, are used for the treatment and/or the prevention of diseases related to the activation of procaspase-3 and/or procaspase-7.

The present invention also relates to a combination of a compound of formula (I), (II), (II-1), (II-2) or (II-3), or any compound as described above, with one or more agent(s) and/or pharmaceutical composition(s) for its use for the treatment and/or prevention of human neoplasms, such as benign neoplasm, carcinoma and cancer.

The present invention also relates to a method for inducing apoptosis comprising a step of administering a compound of formula (I), (II), (II-1), (II-2) or (II-3), or any compound as defined above, to a patient in need thereof.

The present invention also relates to a method for treating and/or preventing human neoplasms, such as benign neoplasm, carcinoma and cancer comprising a step of administering a compound of formula (I), (II), (II-1), (II-2) or (II-3), or any compound as defined above, to a patient in need thereof.

The present invention also relates to a method for treating and/or preventing abnormal proliferation of cells comprising a step of administering a compound of formula (I), (II), (II-1), (II-2) or (II-3), or any compound as defined above, to a patient in need thereof.

The present invention also concerns a method for preparing the compounds of the invention.

The method of preparation of a compound of formula (I) as defined above, comprises a step of coupling 2,2-dimethyl-3-thiomorpholic acid and a compound of formula (III):

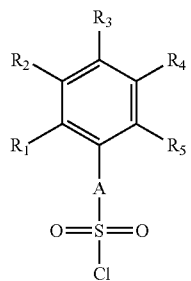
(III)

providing a compound of formula (IV):

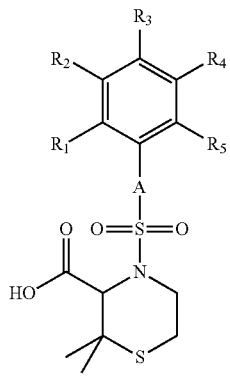
(IV)

wherein A, $R_1$, $R_2$, $R_3$, $R_4$ and $R_5$ are as defined above in formula (I).

According to one embodiment, the coupling reaction is carried out in the presence of a silylating agent.

The preparation of a compound of formula (I) can be carried out according to the following scheme:

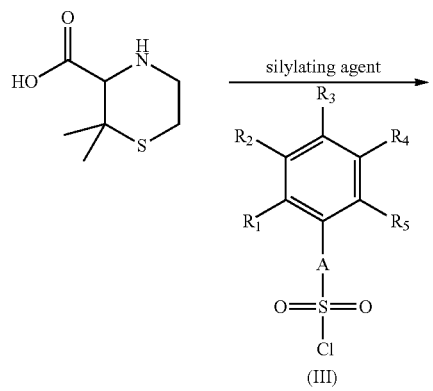

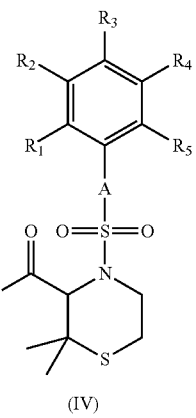
(IV)

According to one embodiment, A is a single bond.

This coupling reaction is for example carried out in an anhydrous solvent, such as anhydrous dichloromethane, but can also be conducted in other solvents, such as chloroform, THF or toluene.

According to one embodiment, 2,2-dimethyl-3-thiomorpholic acid and a silylating agent are for example dissolved in said solvent and the mixture is refluxed for at least one hour.

As suitable silylating agent, one may cite N,O-bis(trimethylsilyl)trifluoroacetamide (BSTFA) or trimethylsilyl chloride.

Then, a tertiary amine base and a solution of sulfonyl chloride (III) (for example in a solvent identical to the above-defined solvent) is added to said mixture, for example at low temperature, for example from –20° C. to 20° C., for example around 0° C. The mixture is then stirred for at least one hour.

As suitable tertiary amine base, one may cite N-methylmorpholine (NMO).

Further to the step of coupling, the method of preparation of the invention also comprises a step of conversion of the compound of formula (IV) into the compound of formula (I), via the preparation of the acid chloride corresponding to (IV).

According to the method of the invention, the compound of formula (IV) can be converted into a compound of formula (I), via the formation of an acid chloride of formula (IV-1):

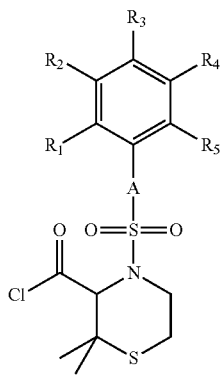
(IV-1)

and the reaction of said acid chloride with hydroxylamine.

The conversion of the compound of formula (IV) to a compound of formula (I) can be carried according to the following scheme:

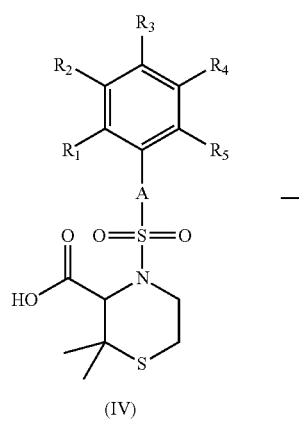

(IV)

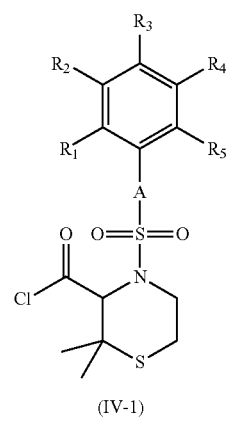

(IV-1)

NH₂OH →

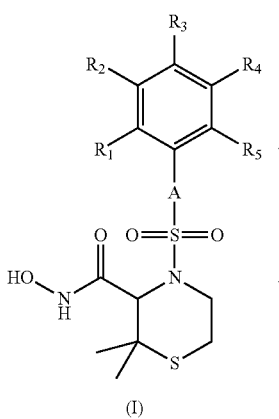

(I)

The reaction of conversion of (IV) into an acid chloride of formula (IV-1) is for example carried out by addition of oxalyl chloride, and a catalytic amount of dimethylformamide (DMF), to the mixture obtained after the step of coupling, for example around 0° C. The resulting mixture is then stirred for at least one hour.

A solution of hydroxylamine (for example at 50% in water) is then dissolved in a solvent, or a mixture of solvent, such as tetrahydrofuran (THF) and water, and is then added to the acid chloride as above prepared, thus yielding the compound of formula (I).

According to one embodiment, the method of preparation of the invention proceeds "one-pot", for example as illustrated in the following scheme:

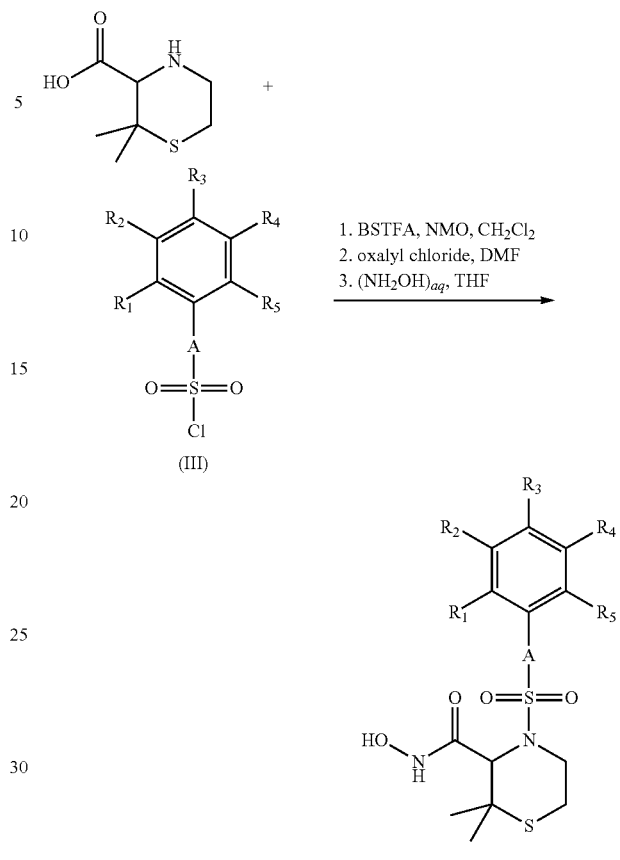

1. BSTFA, NMO, CH₂Cl₂
2. oxalyl chloride, DMF
3. (NH₂OH)$_{aq}$, THF

FIGURES

FIG. 1 represents the percentage of cell growth of human breast tumor SUM149 cells (in vitro), in the presence of compounds 1, 3, 4, 5, 6, 7, 8, 9, 10, 11, 12, 13, and 14 (10 μM concentration).

In FIGS. 2 to 9, compound 1 is represented by rhomb dots, compound 3 is represented by square dots and compound 4 is represented by triangle dots.

EXAMPLES

Figure 1:
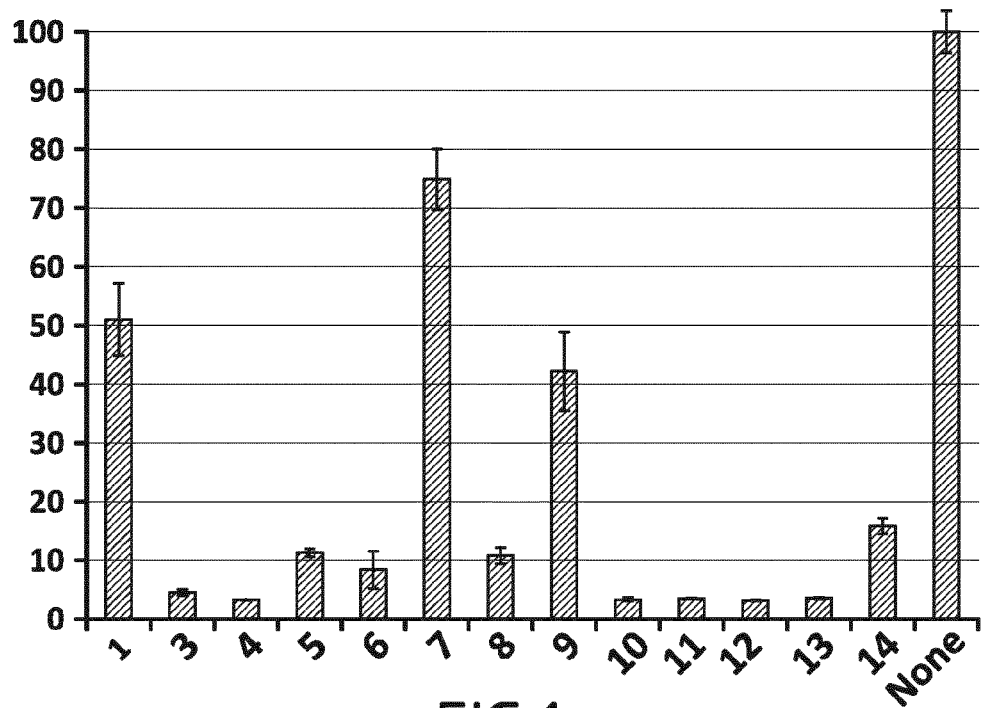

The reactants and solvents used for the synthesis of the compounds 1-14 (Example 1) were commercially purchased at TCI Europe and Sigma Aldrich.

All biological experiments (Examples 2 to 9) have been performed with recommended cell line specific culture medium. For SUM149 and L226, culture medium is supplemented with 10% Fetal Calf Serum. For HME-1 and MCF-10A, culture medium is supplemented with 5% Horse Serum.

Example 1

Synthesis of Compounds 1-14

Compound 1

In a three necked round flask equipped with a condenser was placed at room temperature 2,2-dimethyl-3-thiomorpholic acid (1 mmol) in anhydrous $CH_2Cl_2$ (0.7 mL). The mixture was placed under stirring and refluxed for 10 minutes. N,O-Bis(trimethylsilyl)trifluoroacetamide (BSTFA) (2.05 mmol) was added and the reaction mixture was refluxed for additional 2 hours. N-methylmorpholine (NMO) (155 μL) and phenylsulfonyl chloride (1 mmol) dissolved in $CH_2Cl_2$ (0.35 mL) were subsequently added at 0° C. The reaction mixture was allowed to warm to room temperature whereas the stirring is maintained overnight.

To the resulting solution were added at 0° C. dimethylformamide (DMF) (30 μL) and oxalyl chloride (2.4 mmol). The reaction mixture was allowed to warm to room temperature and stirred for 14 hours.

A hydroxylamine solution (50% in water, 1.45 mL) was dissolved in THF (5 mL) and $H_2O$ (0.35 mL) and rapidly added at 0° C. to the reaction mixture which was allowed to warm to room temperature and stirred for additional 12 hours.

Water was added to allow phase separation. The bottom phase layer was dried over $Na_2SO_4$, filtered and concentrated in vacuo. After removal of the solvents, the crude residue was purified by chromatography on a silica gel column using $CH_2Cl_2$/ethylacetate (1/1) eluent affording expected product (3S)—N-hydroxy-4-(benzenesulfonyl)-2,2-dimethyl-3-thiomorpholine carboxamide (1).

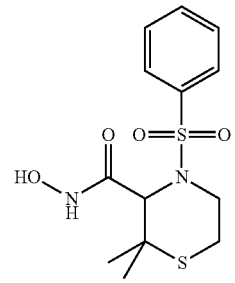

White solid; 1 NMR (DMSO d6): δ=10.78 (s, 1H), 8.01-7.37 (m, 5H), 4.08-3.86 (m, 2H), 2.95-2.56 (m, 5H), 2.14 (s, 3H), 1.45 (s, 3H), 1.23 (s, 3H). $^{13}C$ (DMSO d6): δ=163.93, 139.13, 132.81, 129.24, 126.52, 58.70, 41.15, 30.64, 28.40, 26.52, 23.96. $C_{13}H_{18}N_2O_4S_2$ m/z 331.0781 (100%, (M+H$^+$)).

Compounds 2 to 14 were obtained according to this procedure, using the corresponding starting material sulfonyl chloride.

Compound 2

(3S)—N-hydroxy-4-[(4-methylphenyl)sulfonyl]-2,2-dimethyl-3-thiomorpholine carboxamide (2) was obtained from 2,2-dimethyl-3-thiomorpholic acid and 4-methylphenylsulfonyl chloride, according to the above described procedure.

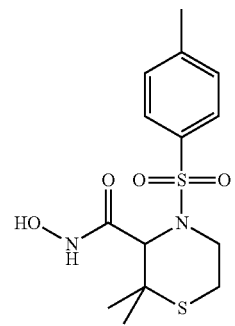

White solid; $^1H$ NMR (acetone d6): δ=10.29 (s, 1H), 8.00 (s, 1H), 7.66 (d, J=7.9 Hz, 2H), 7.37 (d, J=7.9 Hz, 2H), 4.21 (s, 1H), 3.99 (td, J=12.6 and 2.7 Hz, 1H), 3.90 (dt, J=12.6 and 3.5 Hz, 1H), 3.04 (ddd, J=13.7, 12.6 and 3.5 Hz, 1H), 2.52 (dt, J=13.7 and 2.7 Hz, 1H), 2.42 (s, 3H), 1.51 (s, 3H), 1.26 (s, 3H). $^{13}C$ (acetone d6): δ=165.18, 144.15, 137.82, 130.39, 127.86, 60.73, 42.33, 40.34, 29.06, 27.17, 25.27, 21.39. $C_{14}H_{20}N_2O_4S_2$ m/z 345.0943 (100%, (M+H$^+$)).

Compound 3

(3S)—N-hydroxy-4-[(4-isopropylphenyl)sulfonyl]-2,2-dimethyl-3-thiomorpholine carboxamide (3) was obtained from 2,2-dimethyl-3-thiomorpholic acid and 4-isopropylphenylsulfonyl chloride, according to the above described procedure.

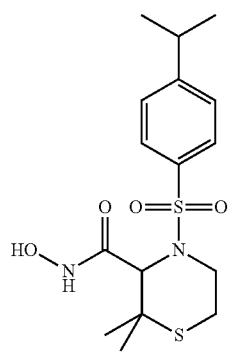 [SMILES: CC(C)c1ccc(S(=O)(=O)N2CCSC(C)(C)C2C(=O)NO)cc1]

White solid; $^1$H NMR (DMSO d6): δ=10.70 (s, 1H), 8.90 (s, 1H), 7.64-7.62 (d, 2H), 7.45-7.43 (d, 2H), 3.97 (t, J=6 Hz, 2H), 3.74-3.71 (m, 1H), 3.00-2.87 (m, 2H), 2.51 (s, 4H), 1.40 (s, 3H), 1.23 (s, 3H), 1.21 (s, 3H), 1.17 (m, 3H). $^{13}$C (DMSO d6): δ=164.11, 153.49, 136.80, 127.16, 126.78, 58.62, 41.06, 33.28, 28.43, 26.53, 23.96, 2342, 23.35.

Compound 4

(3S)—N-hydroxy-4-[(2,3,5,6-tetramethylphenyl)sulfonyl]-2,2-dimethyl-3-thiomorpholine carboxamide (4) was obtained from 2,2-dimethyl-3-thiomorpholic acid and 2,3,5,6-tetramethylphenylsulfonyl chloride, according to the above described procedure.

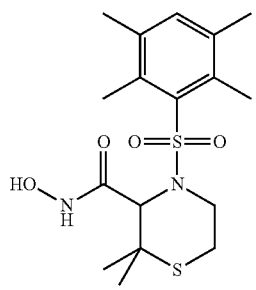

White solid: $^1$H NMR (acetone d6): δ=10.09 (s, 1H), 8.07 (s, 1H), 7.27 (s, 1H), 4.22 (td, J=13.5 and 2.6 Hz, 1H), 4.08 (s, 1H), 3.63 (dt, J=13.8 and 2.9 Hz, 1H), 3.11 (ddd, J=13.5, 12.9 and 3.4 Hz, 1H), 2.49 (s, 6H), 2.47 (dt, J=13.7 and 2.4 Hz, 1H), 2.28 (s, 6H), 1.53 (s, 3H), 1.25 (s, 3H). $^{13}$C (acetone d6): δ=166.14, 137.19, 137.10, 136.77, 59.64, 41.81, 9.93, 29.42, 27.62, 24.62, 20.99, 17.95. $C_{17}H_{26}N_2O_4S_2$ m/z 387.1412 (100%, (M+H$^+$)).

Compound 5

(3S)—N-hydroxy-4-[(4-bromomethylphenyl)sulfonyl]-2,2-dimethyl-3-thiomorpholine carboxamide (5) was obtained from 2,2-dimethyl-3-thiomorpholic acid and 4-bromomethylphenylsulfonyl chloride, according to the above described procedure.

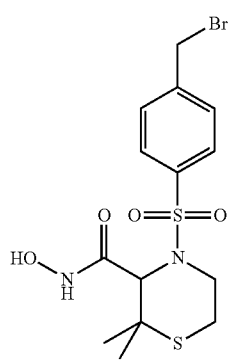

Yellow solid; $^1$H NMR (DMSO d6): δ=9.02 (m, 2H), 8.12-8.10 (m, 2H), 7.53-7.51 (m, 2H), 4.41 (s, 2H), 2.93-2.67 (m, 2H), 1.48 (s, 3H), 1.27 (s, 3H). $^{13}$C (DMSO d6): δ=166.30, 144.09, 142.54, 131.26, 128.42, 68.31, 56.44, 49.13, 33.00, 27.26, 25.38, 22.51.

Compound 6

(3S)—N-hydroxy-4-[(4-trifluoromethylphenyl)sulfonyl]-2,2-dimethyl-3-thiomorpholine carboxamide (6) was obtained from 2,2-dimethyl-3-thiomorpholic acid and 4-trifluoromethylphenylsulfonyl chloride, according to the above described procedure.

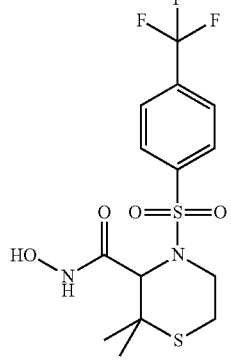

White solid; 1H NMR (DMSO d6): δ=10.71 (s, 1H), 9.83 (s, 1H), 8.06-7.06 (m, 4H), 3.98-3.78 (m, 3H), 2.99-2.55 (m, 2H), 1.41 (s, 3H), 1.17 (s, 3H). 13C (DMSO d6): δ=163.55, 159.55, 142.66, 132.59, 130.32, 129.08, 128.76, 127.54, 126.43, 126.11, 124.77, 122.06, 119.94, 117.65, 65.27, 58.91, 54.29, 41.46, 28.33, 26.48, 23.92.

Compound 7

(3S)—N-hydroxy-4-[(4-fluorophenyl)sulfonyl]-2,2-dimethyl-3-thiomorpholine carboxamide (7) was obtained from 2,2-dimethyl-3-thiomorpholic acid and 4-fluorophenylsulfonyl chloride, according to the above described procedure.

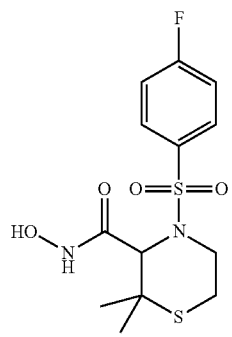 [SMILES: CC1(C)SCCN(S(=O)(=O)c2ccc(F)cc2)C1C(=O)NO]

White solid; $^1$H NMR (DMSO d6): δ=9.65 (s, 2H), 8.00-7.97 (m, 2H), 7.19-7.15 (m, 3H), 4.62-3.89 (m, 2H), 2.81-2.67 (m, 2H), 1.48 (s, 3H), 1.39 (s, 3H). $^{13}$C (DMSO d6): δ=165.54, 163.72, 159.62, 135.24, 130.11, 130.01, 129.66, 129.56, 116.50, 116.27, 116.17, 115.95, 64.51, 58.78, 48.56, 28.38, 26.51, 23.97.

Compound 8

(3S)—N-hydroxy-4-[(4-ethylphenyl)sulfonyl]-2,2-dimethyl-3-thiomorpholine carboxamide (8) was obtained from 2,2-dimethyl-3-thiomorpholic acid and 4-ethylphenylsulfonyl chloride, according to the above described procedure.

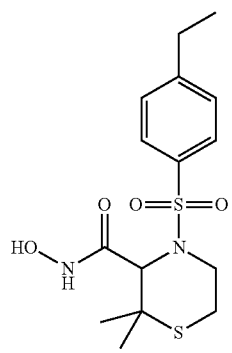 [SMILES: CCc1ccc(S(=O)(=O)N2CCSC(C)(C)C2C(=O)NO)cc1]

White solid; $^1$H NMR (DMSO d6): δ=10.72 (s, 1H), 8.91 (s, 1H), 7.62 (d, J=6.0 Hz, 2H), 7.38 (d, J=6.0 Hz, 2H), 4.05 (s, 1H), 3.99-3.71 (m, 4H), 2.86-2.66 (m, 2H), 2.50 (s, 3H), 1.38 (s, 3H), 1.16 (s, 3H). $^{13}$C (DMSO d6): δ=164.09, 149.04, 136.53, 128.53, 126.70, 58.64, 41.04, 28.39, 27.92, 26.50, 23.94, 14.93.

Compound 9

(3S)—N-hydroxy-4-[(diphenyl ethanesulfonyl]-2,2-dimethyl-3-thiomorpholine carboxamide (9) was obtained from 2,2-dimethyl-3-thiomorpholic acid and diphenyl ethanephenylsulfonyl chloride, according to the above described procedure.

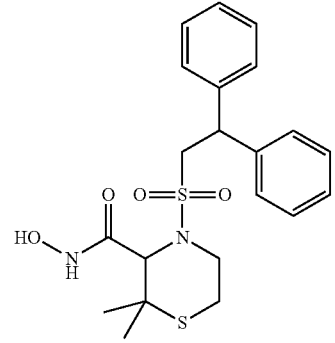 [SMILES: CC1(C)SCCN(S(=O)(=O)CC(c2ccccc2)c2ccccc2)C1C(=O)NO]

White solid; $^1$H NMR (DMSO d6): δ=7.80 (s, 1H), 7.27-7.02 (m, 10H), 5.54 (s, 1H), 4.53-4.47 (m, 2H), 3.90 (d, J=6 Hz, 2H), 3.72-3.65 (m, 1H), 2.87 (td, J=13.5 and 2.6 Hz, 1H), 2.55-2.49 (m, 1H), 2.06-1.95 (m, 1H), 1.43 (s, 3H), 1.01 (m, 3H). $^{13}$C (DMSO d6): δ=160.91, 142.28, 141.90, 140.66, 128.84, 128.69, 127.59, 126.96, 126.74, 57.15, 51.31, 46.52, 46.15, 43.27, 39.69, 26.39, 26.26, 15.03.

Compound 10

(3S)—N-hydroxy-4-[(4-dodecyl)phenylsulfonyl]-2,2-dimethyl-3-thiomorpholine carboxamide (10) was obtained from 2,2-dimethyl-3-thiomorpholic acid and 4-dodecylphenylsulfonyl chloride, according to the above described procedure.

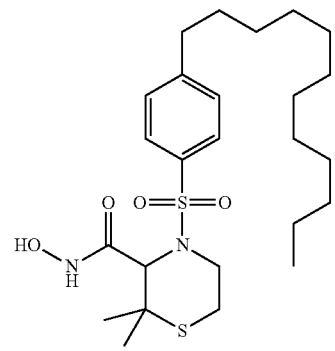 [SMILES: CCCCCCCCCCCCc1ccc(S(=O)(=O)N2CCSC(C)(C)C2C(=O)NO)cc1]

Pale yellow viscous oil; $^1$H NMR (DMSO d6): δ=7.80 (d, 2H), 7.24 (d, 2H), 6.75 (s, 1H), 4.37 (d, J=6 Hz, 1H), 3.90-3.51 (m, 1H), 3.12-2.39 (m, 2H), 1.56-0.73 (m, 35H). $^{13}$C (DMSO d6): δ=165.37, 154.82, 153.57, 133.03, 128.72, 128.36, 127.75, 65.95, 61.27, 48.01, 46.23, 40.09, 39.71, 38.08, 36.59, 31.83, 29.64, 29.28, 27.53, 26.49, 22.66, 21.88, 19.33, 15.05, 14.10, 12.08.

Compound 11

(3S)—N-hydroxy-4-[(2,4,6-trimethylphenyl)sulfonyl]-2,2-dimethyl-3-thiomorpholine carboxamide (11) was obtained from 2,2-dimethyl-3-thiomorpholic acid and 2,4,6-trimethylphenylsulfonyl chloride, according to the above described procedure.

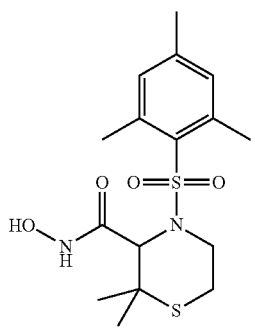 [SMILES: Cc1cc(C)c(S(=O)(=O)N2CCSC(C)(C)C2C(=O)NO)c(C)c1]

White solid; $^1$H NMR (acetone d6): δ=10.15 (s, 1H), 8.16 (s, 1H), 7.05 (s, 2H), 4.22 (td, J=13.2 and 2.3 Hz, 1H), 4.07 (s, 1H), 3.68 (dt, J=13.2 and 2.7 Hz, 1H), 3.12 (ddd, J=13.9, 13.2 and 2.7 Hz, 1H), 2.57 (s, 6H), 2.51 (dt, J=13.9 and 2.3 Hz, 1H), 2.30 (s, 3H), 1.52 (s, 3H), 1.26 (s, 3H). $^{13}$C (acetone d6): δ=165.94, 143.54, 140.98, 132.77, 60.14, 41.94, 39.99, 29.46, 27.56, 24.79, 22.98, 20.82. $C_{16}H_{24}N_2O_4S_2$ m/z 372.1177 (100%, (M+H$^+$)).

Compound 12

(3S)—N-hydroxy-4-[(2,3,4,5,6-pentamethylphenyl)sulfonyl]-2,2-dimethyl-3-thiomorpholine carboxamide (12) was obtained from 2,2-dimethyl-3-thiomorpholic acid and 2,3,4,5,6-pentamethylphenylsulfonyl chloride, according to the above described procedure.

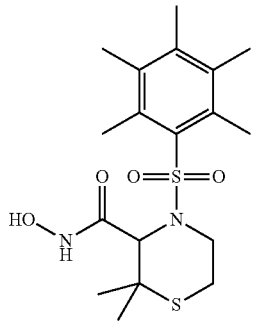 [SMILES: Cc1c(C)c(C)c(S(=O)(=O)N2CCSC(C)(C)C2C(=O)NO)c(C)c1C]

Whites solid; $^1$H NMR (acetone d6): δ=10.10 (s, 1H), 8.12 (s, 1H), 4.19 (td, J=13.0 and 2.6 Hz, 1H), 4.11 (s, 1H), 3.59 (dt, J=13.6 and 3.3 Hz, 1H), 3.09 (ddd, J=13.6, 13.0 and 3.3 Hz, 1H), 2.52 (s, 6H), 2.45 (dt, J=13.6 and 2.6 Hz, 1H), 2.31 (s, 3H), 2.25 (s, 6H), 1.55 (s, 3H), 1.25 (s, 3H). $^{13}$C (acetone d6): δ=165.87, 140.84, 138.48, 135.68, 135.42, 59.74, 41.95, 40.00, 29.56, 27.59, 24.75, 19.02, 17.87, 17.12. $C_{18}H_{28}N_2O_4S_2$ m/z 400.1490 (100%, (M+H$^+$)).

Compound 13

(3S)—N-hydroxy-4-[(4-propylphenyl)sulfonyl]-2,2-dimethyl-3-thiomorpholine carboxamide (13) was obtained from 2,2-dimethyl-3-thiomorpholic acid and 4-propylphenylsulfonyl chloride, according to the above described procedure.

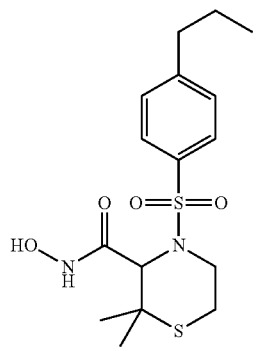 [SMILES: CCCc1ccc(S(=O)(=O)N2CCSC(C)(C)C2C(=O)NO)cc1]

White solid; $^1$H NMR (acetone d6): δ=10.29 (s, 1H), 8.00 (s, 1H), 7.69 (d, J=8.3 Hz, 2H), 7.39 (d, J=8.3 Hz, 2H), 4.21 (s, 1H), 4.00 (td, J=12.3 and 2.5 Hz, 1H), 3.90 (dt, J=12.3 and 4.0 Hz, 1H), 3.09 (ddd, J=13.8, 12.3 and 4.0 Hz, 1H), 2.69 (t, J=7.5 Hz, 2H), 2.52 (dt, J=13.8 and 2.5 Hz, 1H), 1.67 (quint, J=7.5 Hz, 2H), 1.50 (s, 3H), 1.26 (s, 3H), 0.94 (t, J=7.5 Hz, 3H). $^{13}$C (acetone d6): δ=165.23, 148.73, 138.05, 129.86, 127.91, 60.73, 42.36, 40.31, 38.24, 29.54, 27.19, 25.27, 24.86, 13.88. $C_{16}H_{24}N_2O_4S_2$ m/z 372.1177 (100%, (M+H$^+$)).

Compound 14

(3S)—N-hydroxy-4-[(3,5-dimethylphenyl)sulfonyl]-2,2-dimethyl-3-thiomorpholine carboxamide (14) was obtained from 2,2-dimethyl-3-thiomorpholic acid and 3,5-dimethylphenylsulfonyl chloride, according to the above described procedure.

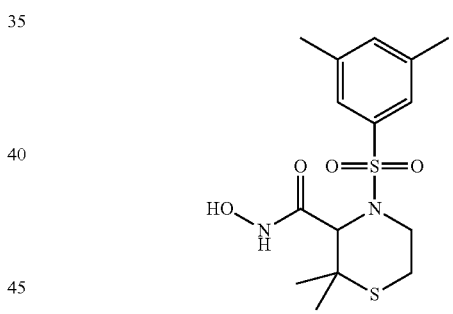

White solid; $^1$H NMR (acetone as): δ=10.35 (s, 1H), 7.97 (s, 1H), 7.39 (s, 2H), 7.26 (s, 1H), 4.18 (s, 1H), 3.97 (td, J=12.2 and 2.8 Hz, 1H), 3.90 (ddd, J=12.2, 4.3 and 2.8 Hz, 1H), 3.04 (ddd, J=13.6, 12.2 and 4.3 Hz, 1H), 2.51 (dt, J=13.6 and 2.8 Hz, 1H), 2.37 (s, 6H), 1.52 (s, 3H), 1.25 (s, 3H). $^{13}$C (acetone d6): δ=165.01, 140.30, 139.85, 124.92, 125.36, 60.79, 42.36, 40.39, 29.32, 27.24, 25.33, 21.19. $C_{15}H_{22}N_2O_4S_2$ m/z 358.1021 (100%, (M+H$^+$)).

Example 2

Inhibition of Tumor Cell Growth

Human breast tumor SUM149 cells (Inflammatory Breast Cancer (IBC) of basal subtype) were plated in a 96 well plate at 3000 cells/100 μL at 37° C. in 5% $CO_2$. Compounds 1, 3, 4, 5, 6, 7, 8, 9, 10, 11, 12, 13, 14 at 10 μM were added at day 0 and day 3. The number of viable cells was determined in triplicate at day 5 by incubating 10 μL of the alamar blue staining solution for 2 hours at 37° C. (FIG. 1).

Example 3

Inhibition of Tumor Cell Growth

Figure 2:
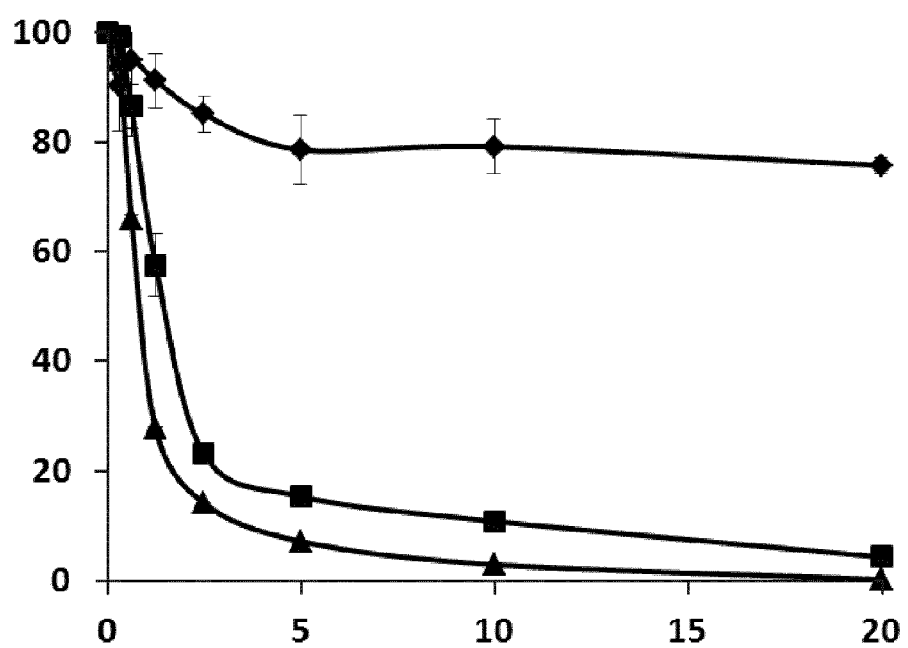
FIG. 2 represents the percentage of cell growth of human breast tumor SUM149 cells (in vitro), according to drug concentration (μM).

Human breast tumor SUM149 cells were plated in a 96 well plate at 3000 cells/100 µL at 37° C. in 5% $CO_2$. Serial dilutions of drugs (compounds 1, 3 or 4) ranging from 20 µM to 300 nM were added at day 0 and day 3. The number of viable cells was determined in triplicate at day 5 by incubating 10 µL of the alamar blue staining solution for 2 hours at 37° C. (FIG. 2).

Figure 3:
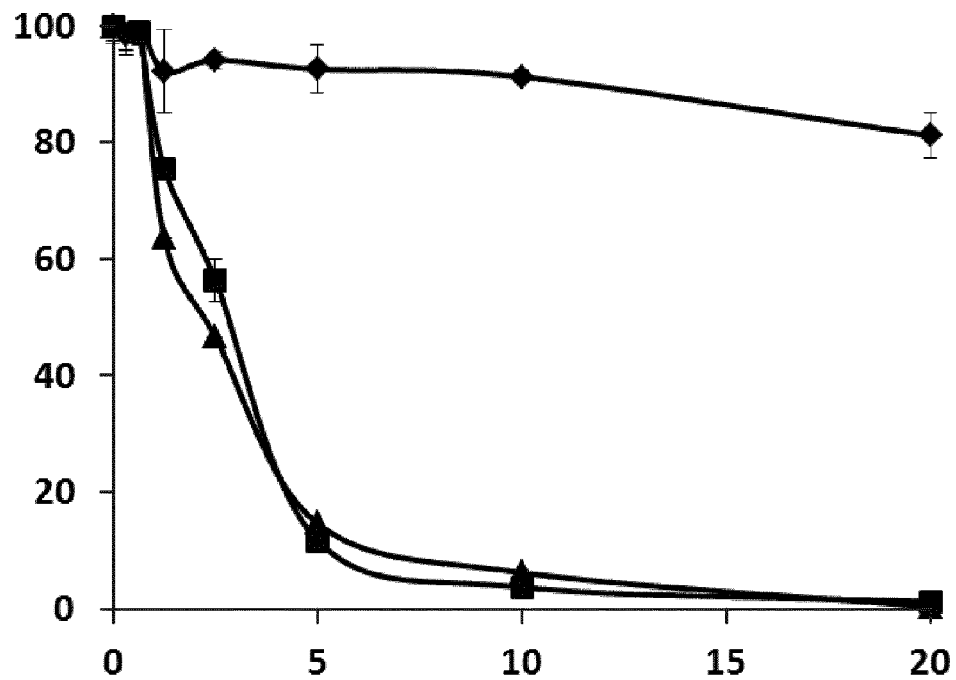
FIG. 3 represents the percentage of cell growth of human breast tumor L226 cells (in vitro), according to drug concentration (μM).

Human breast tumor L226 cells (Inflammatory Breast Cancer (IBC) of ERB-B2 subtype) were plated in a 96 well plate at 3000 cells/100 µL at 37° C. in 5% $CO_2$. Serial dilutions of drugs (compounds 1, 3 or 4) ranging from 20 µM to 300 nM were added at day 0 and day 3. The number of viable cells was determined in triplicate at day 5 by incubating 10 µL of the alamar blue staining solution for 2 hours at 37° C. (FIG. 3).

Example 4

Effect on Growth of Normal Cells

Figure 4:
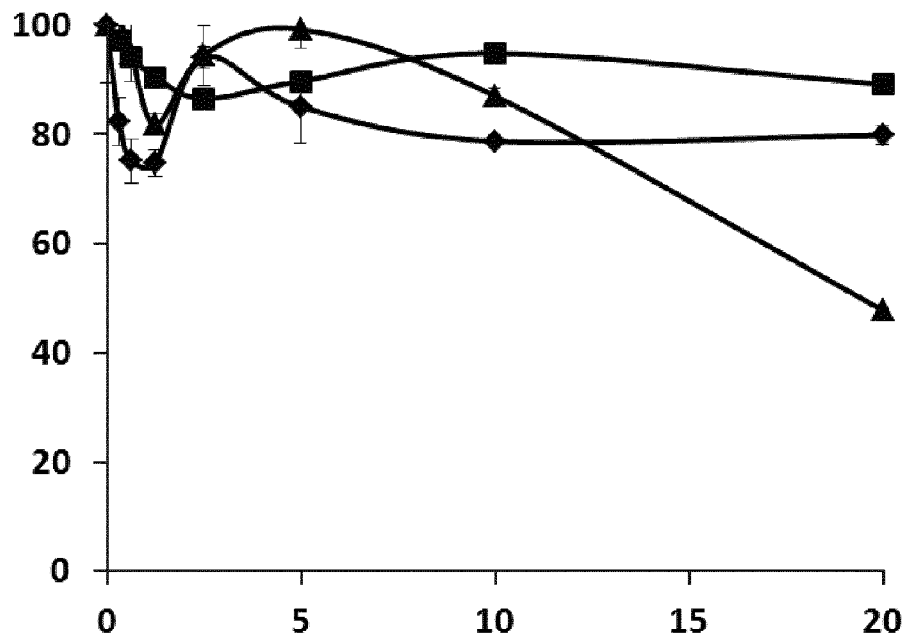
FIG. 4 represents the percentage of cell growth of human normal mammary epithelial HME-1 cells (in vitro), according to drug concentration (μM).

Human normal mammary epithelial HME-1 cells were plated in a 96 well plate at 3000 cells/100 µL at 37° C. in 5% $CO_2$. Serial dilutions of drugs (compounds 1, 3 or 4) ranging from 20 µM to 300 nM were added at day 0 and day 3. The number of viable cells was determined in triplicate at day 5 by incubating 10 µL of the alamar blue staining solution for 2 hours at 37° C. (FIG. 4).

Figure 5:
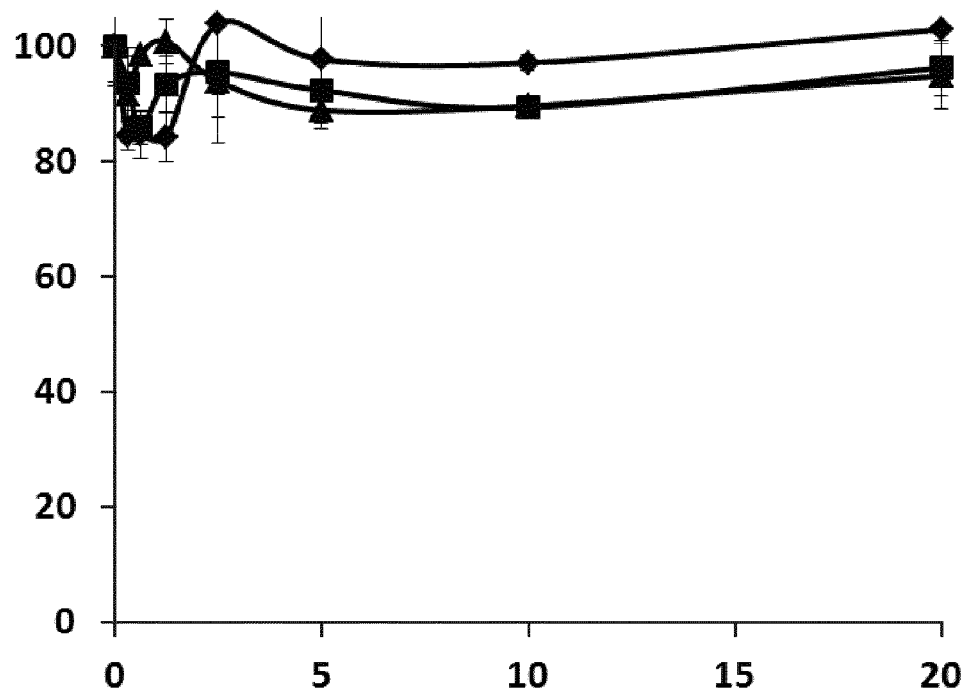
FIG. 5 represents the percentage of cell growth of human normal mammary epithelial MCF10-A cells (in vitro), according to drug concentration (μM).

Human normal mammary epithelial MCF-10A cells were plated in a 96 well plate at 3000 cells/100 µL at 37° C. in 5% $CO_2$. Serial dilutions of drugs (compounds 1, 3 or 4) ranging from 20 µM to 300 nM were added at day 0 and day 3. The number of viable cells was determined in triplicate at day 5 by incubating 10 µL of the alamar blue staining solution for 2 hours at 37° C. (FIG. 5).

Example 5

Induction of Active Caspase-3 and Caspase-7 in Tumor Cells

Figure 6:
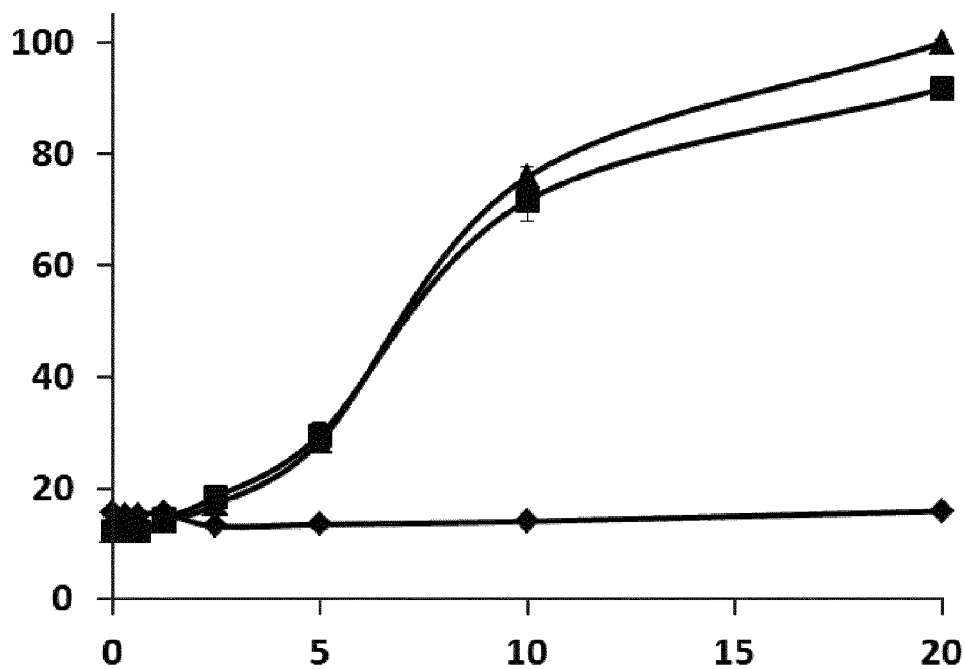
FIG. 6 represents the percentage of active caspase-3 and caspase-7 in human breast tumor SUM149 cells (in vitro), according to drug concentration (μM).

Human breast tumor SUM149 cells were plated in a 96 well plate at 10000 cells/100 µL at 37° C. in 5% $CO_2$. Serial dilutions of drugs (compounds 1, 3 or 4) ranging from 20 µM to 300 nM were added at day 0. Active caspase-3 and caspase-7 were measured in triplicate after 24 h treatment by incubating 50 µL of the Caspase-Glo 3/7 reagent for 60 min at 25° C. This reagent containing the proluminescent tetrapeptide sequence DEVD in a cell lysis buffer (Promega) (FIG. 6).

Figure 7:
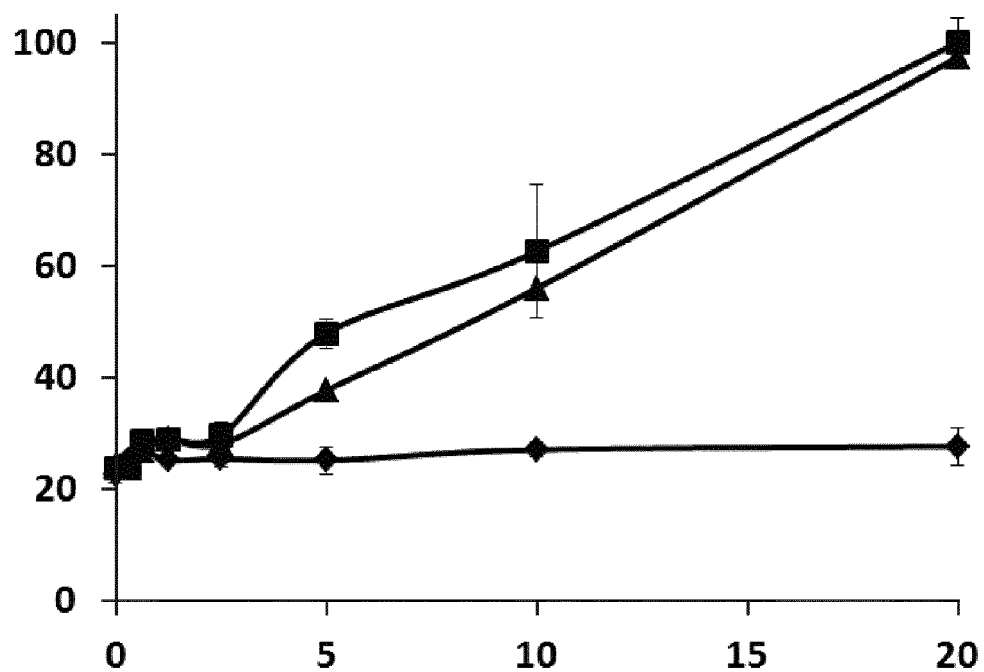
FIG. 7 represents the percentage of active caspase-3 and caspase-7 in human breast tumor L226 cells (in vitro), according to drug concentration (μM).

Human breast tumor L226 cells were plated in a 96 well plate at 10000 cells/100 µL at 37° C. in 5% $CO_2$. Serial dilutions of drugs (compounds 1, 3 or 4) ranging from 20 µM to 300 nM were added at day 0. Active caspase-3 and caspase-7 were measured in triplicate after 24 h treatment by incubating 50 µL of the Caspase-Glo 3/7 reagent for 60 min at 25° C. This reagent containing the proluminescent tetrapeptide sequence DEVD in a cell lysis buffer (Promega) (FIG. 7).

Example 6

Induction of Active Caspase-3 and Caspase-7 in Normal Cells

Figure 8:
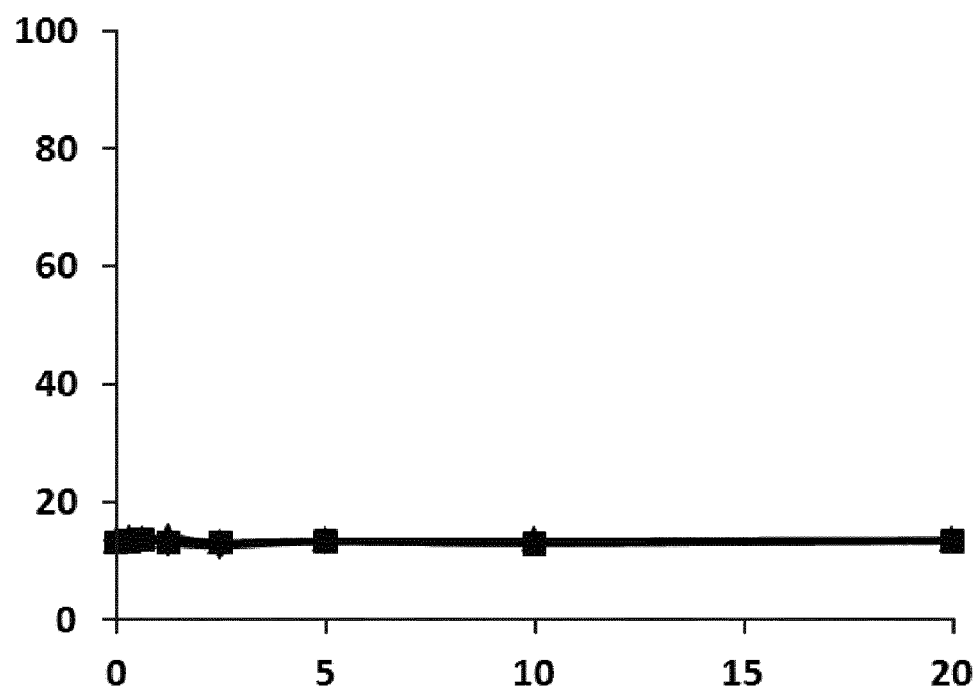
FIG. 8 represents the percentage of active caspase-3 and caspase-7 in human normal mammary epithelial HME-1 cells (in vitro), according to drug concentration (μM).

Human normal mammary epithelial HME-1 cells were plated in a 96 well plate at 10000 cells/100 µL at 37° C. in 5% $CO_2$. Serial dilutions of drugs (compounds 1, 3 or 4) ranging from 20 µM to 300 nM were added at day 0. Active caspase-3 and caspase-7 were measured in triplicate after 24 h treatment by incubating 50 µL of the Caspase-Glo 3/7 reagent for 60 min at 25° C. This reagent containing the proluminescent tetrapeptide sequence DEVD in a cell lysis buffer (Promega) (FIG. 8).

Figure 9:
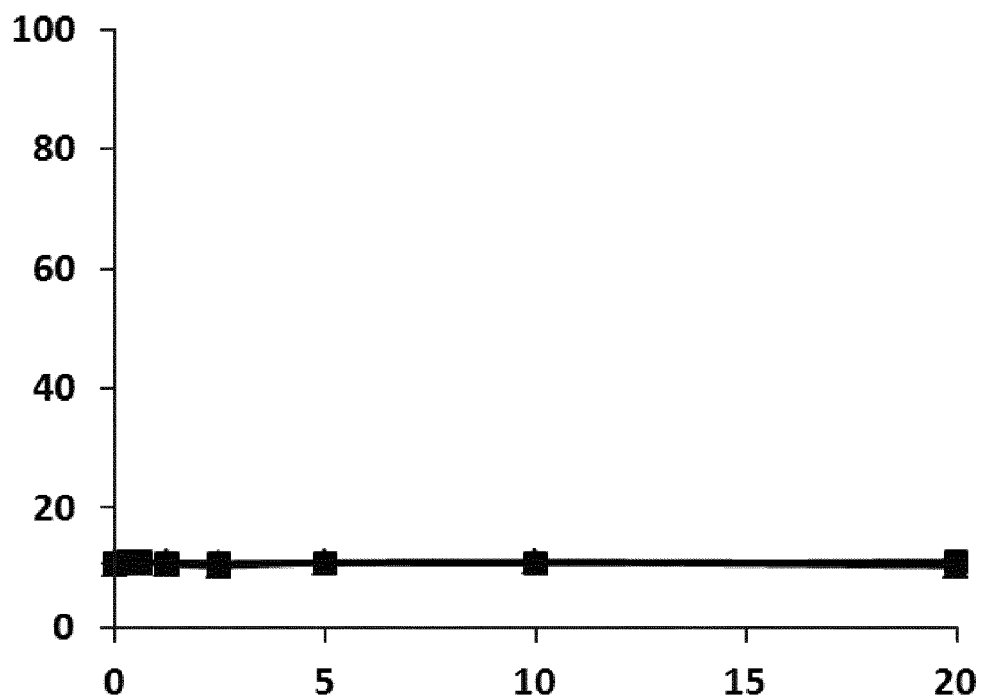
FIG. 9 represents the percentage of active caspase-3 and caspase-7 in human normal mammary epithelial MCF10-A cells (in vitro), according to drug concentration (μM).

Human normal mammary epithelial MCF-10A cells were plated in a 96 well plate at 10000 cells/100 µL at 37° C. in 5% $CO_2$. Serial dilutions of drugs (compounds 1, 3 or 4) ranging from 20 µM to 300 nM were added at day 0. Active caspase-3 and caspase-7 were measured in triplicate after 24 h treatment by incubating 50 µL of the Caspase-Glo 3/7 reagent for 60 min at 25° C. This reagent containing the proluminescent tetrapeptide sequence DEVD in a cell lysis buffer (Promega) (FIG. 9).

Example 7

Figure 10:
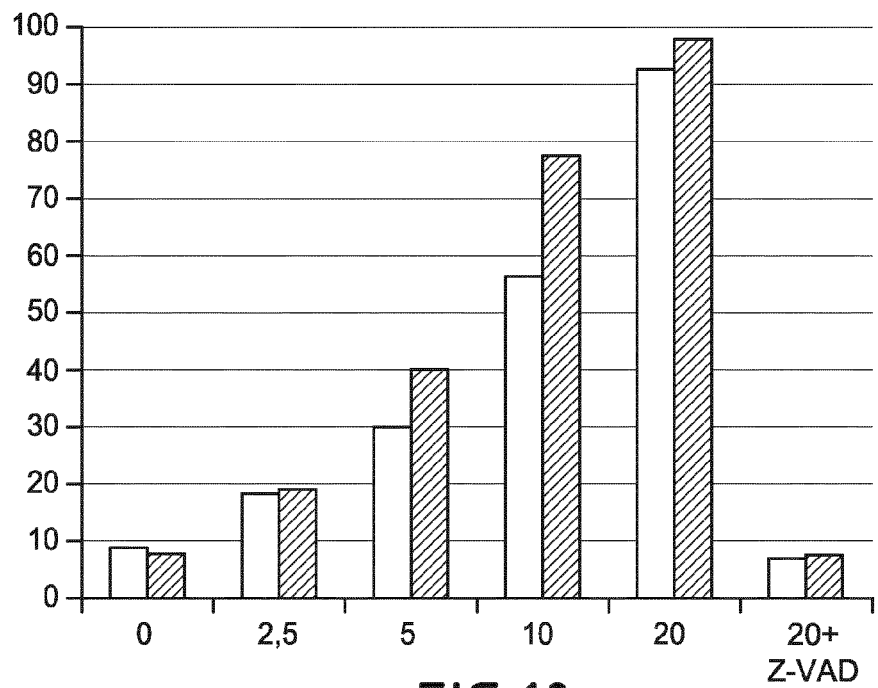
FIG. 10 represents the percentage of Annexin V positive cells (human breast tumor SUM149), according to drug concentration (μM, white column=compound 3, striped column=compound 4), with or without Z-VAD treatment.

Inhibition of Caspases Fully Blocks Compound 3 and Compound 4 Induced Apoptosis Human breast tumor SUM149 cells were plated in dishes at a concentration of $10^6$ cells/5 µL Cells were treated with compound 3 or compound 4 (2.5 to 20 µM) for 48 h, with or without Z-VAD-FMK, a pan-caspases inhibitor. Cells were double stained with annexinV-FITC and 7-AAD to measure cell apoptosis. Z-VAD treatment fully impaired compound 3 and compound 4 induced apoptosis (FIG. 10).

Example 8

IC50 values of compounds 1-14 for the inhibition of SUM149 and L226 tumor cells growth were measured (according to the experimental procedure of Examples 2 and 3):

|        | 1   | 3   | 4   | 5   | 6   | 7   | 8   | 9   | 10  | 11  | 12  | 13  | 14  |
|--------|-----|-----|-----|-----|-----|-----|-----|-----|-----|-----|-----|-----|-----|
| SUM149 | 20  | 2.5 | 2.5 | 2.5 | 2.5 | 20  | 7.5 | 10  | 2.5 | 2.5 | 2.5 | 2.5 | 5   |
| L226   | >20 | 2.5 | 2.5 | 20  | 5   | —   | 5   | —   | 3.5 | 2.5 | 2   | 2.5 | —   |

IC50 values were calculated on the basis of cell growth inhibition (—) not tested IC50 values of compounds 1-14 for the inhibition of MCF-10A and HME-1 normal cells growth were also measured (according to the experimental procedure of Examples 4 and 5):

|        | 1   | 3   | 4   | 5   | 6   | 7 | 8   | 9 | 10  | 11  | 12  | 13  | 14 |
|--------|-----|-----|-----|-----|-----|---|-----|---|-----|-----|-----|-----|----|
| MCF-10A| >20 | >20 | 20  | >20 | >20 | — | >20 | — | 20  | 20  | 15  | >20 | —  |
| HME-1  | >20 | >20 | >20 | >20 | >20 | — | >20 | — | >20 | >20 | >20 | >20 | —  |

IC50 values were calculated on the basis of cell growth inhibition
(—) not tested These results show that compounds 1 to 14 according to the present invention selectively inhibit the growth of tumor cells, without affecting the growth of normal cells.

Example 9

Caspase 3/7 activation in SUM149 and L226 tumor cells was measured.
The calculated values R correspond to Relative Luminescence Units (RLU) fold increase from untreated cells (R=RLU at 20 μM/RLU at 0 μM).

|        | 1 | 3   | 4   | 5   | 6   | 7 | 8   | 9 | 10  | 11  | 12  | 13  | 14 |
|--------|---|-----|-----|-----|-----|---|-----|---|-----|-----|-----|-----|----|
| SUM149 | 1 | 6.3 | 4.4 | 5.5 | 5.9 | — | 5.7 | — | 5.5 | 6.4 | 6.8 | 5.4 | —  |
| L226   | 1 | 2.1 | 7.4 | 3.2 | 2.8 | — | 2.3 | — | 8.9 | 8.7 | 6.2 | 5.8 | —  |

(—) not tested

Caspase 3/7 activation in MCF-10A and HME-1 normal cells was also measured.

|        | 1 | 3 | 4 | 5   | 6   | 7 | 9 | 10  | 11 | 12  | 13  | 14  | 15  | 16 |
|--------|---|---|---|-----|-----|---|---|-----|----|-----|-----|-----|-----|----|
| MCF-10A| 1 | 1 | 1 | 1   | 1   | — | — | 1.1 | —  | 1.1 | 1.1 | 1.1 | 0.9 | —  |
| HME-1  | 1 | 1 | 1 | 1.1 | 0.9 | — | — | 0.8 | —  | 1.2 | 1.2 | 1.1 | 1.1 | —  |

(—) not tested

These results show that compounds 1 to 16 according to the present invention induce higher caspase 3/7 activation in tumor cells than in normal cells.

Example 10

Inhibition of Tumor Cell Growth, Influence of Culture Medium Composition

Figure 11:
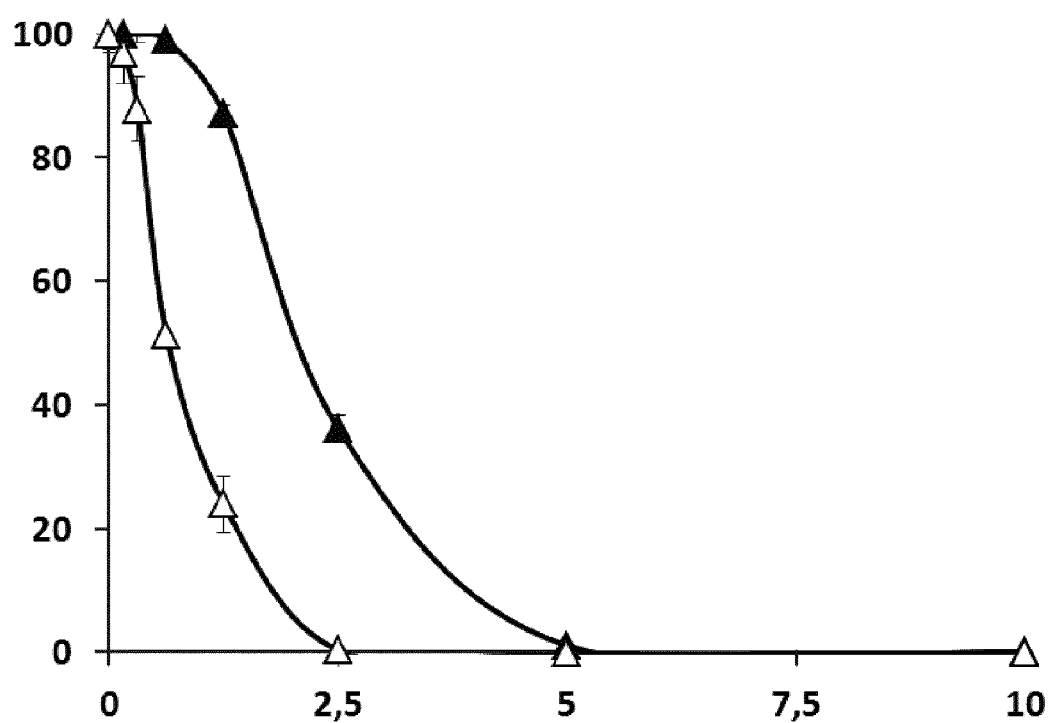
FIG. 11 represents the percentage of cell growth of human breast tumor SUM149 cells (in vitro), according to drug concentration of compound 4 (μM), with (recommended medium, black triangle dots) or without Fetal Calf Serum (synthetic medium, white triangle dots).

Human breast tumor SUM149 cells were plated in a 96 well plate at 3000 cells/100 μL at 37° C. in 5% $CO_2$ in recommended medium containing 10% FCS or in synthetic medium without FCS. Serial dilutions of drug (compound 4) ranging from 10 μM to 0.16 μM were added at day 0 and day 3. The number of viable cells was determined in triplicate at day 5 by incubating 10 μL of the alamar blue staining solution for 2 hours at 37° C. (FIG. 11). The IC50 in recommended medium containing 10% FCS was measured at 2 μM, while it was measured at 0.6 μM without FCS.

Example 11

High Throughput Cell Growth Analysis of 14 Compounds on 33 Different Cell Models Thirty eight validated cells lines, including BXPC3 cells, DU145 cells, OPM2 cells, U-2-OS cells, PLCPRF5 cells, A549 cells, SUM149 cells, HepG2 cells, L389 cells, HGC27 cells, TOV-112D cells, Messa cells, Karpas 299 cells, A498 cells, HCT-116 cells, H1299 cells, Hep2 cells, DLD1 cells, HUT78 cells, AGS cells, A4573 cells, ACHN cells, Panc-1 cells, A375 cells, BT-20 cells, L226 cells, MDAMB231 cells, U118 cells, PC-3 cells, SW579 cells, CLS354-4 cells, Calu-6 cells, U87MG cells, MeWO cells, HUVEC, HME-1 cells, MCF10-A cells and fibroblasts, were plated at 3000 cells/100 μL at 37° C. in 5% $CO_2$ in recommended medium containing 10% FCS.

Compounds 12, 4, 11, 3, 13, 6, 8, 14, 1 and 7, described in the above examples, and DMSO as a control, were tested at various concentrations and % inhibition of cell growth at 10 μM was more particularly studied.

Unsupervised hierarchical clustering of these results was determined and showed variable efficiency of these compounds according cell line sensitivity. It was in particular observed that compound 12 was the most effective both qualitatively (IC50<1 μM) and quantitatively (86% of cell lines studied were sensitive).

Additionally, it was advantageously observed that non tumoral cell lines (HUVEC, HME-1 cells, MCF10-A cells and fibroblasts) were resistant to all the compounds studied.

Example 12

Compound 12 Inhibits Cancer Stem Cells Compartment

Cancer stem cells (CSCs) are thought to contribute to tumor initiation, maintenance, resistance to therapy, and metastasis progression. Treatment with drugs enrich in resistant CSCs. In vitro, breast CSCs express high level of aldehyde dehydrogenase-1 (ALDH1), which can be detected by using a commercial assay (CSCs are "Aldefluor" positive). Briefly, cells were incubated in Aldefluor assay buffer containing ALDH substrate (BAAA (BODIPY®—aminoacetaldehyde), 1 μmol/L per $1 \times 10^6$ cells). Negative control was done in the presence of diethylaminobenzaldehyde (DEAB), a specific ALDH inhibitor. Cells were then incubated for 40 min at 37° C. Cells were analyzed with the LSRII flow cytometer (Becton-Dickinson). PI (Propidium Iodide) exclusion was used to gate viable cells.

Figure 12:
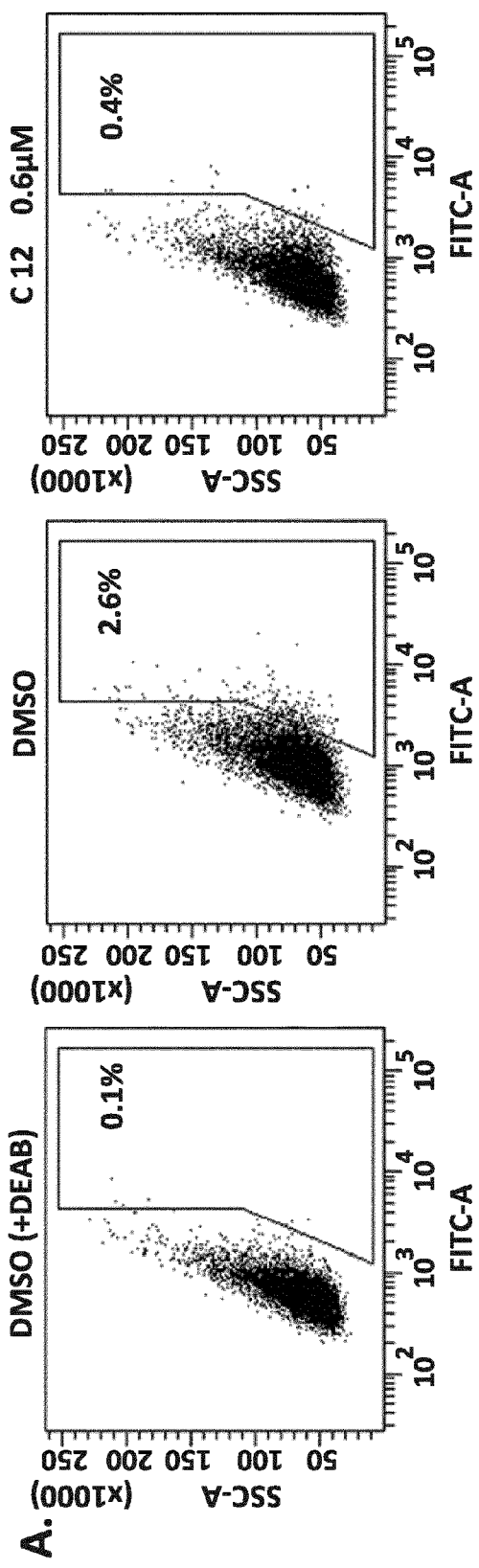
FIG. 12A shows the results of a FACS analysis of cells treated with diethylaminobenzaldehyde (DEAB) in DMSO as a negative control, with DMSO alone or with Compound 12 (0.6 μM) in DMSO, and incubated in Aldefluor assay buffer containing ALDH substrate to determine the percentage of cancer stem cells.
FIG. 12B shows histograms representing the ratio between the percentage of ALDH+ cells in populations of cells treated with Compound 12 (C12) or doxorubicin, and the percentage of ALDH+ cells in populations of cells in DMSO.
Figure 12:
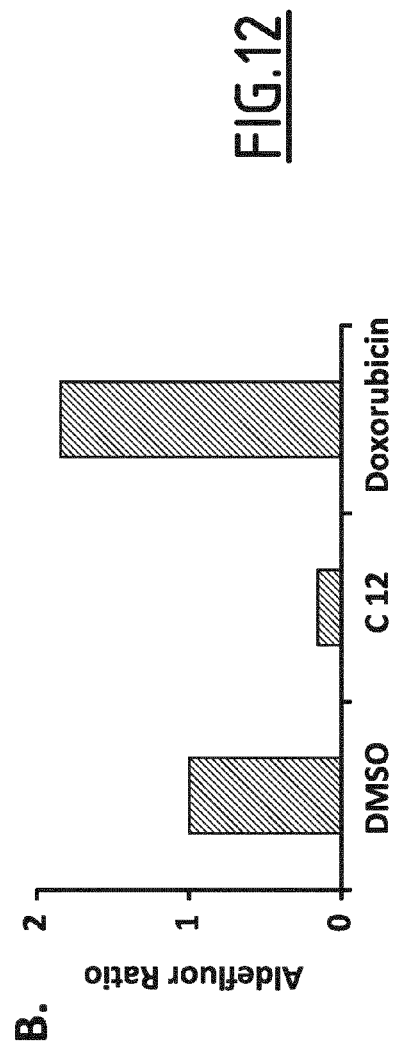

Treatment with 0.6 μM reduced the pool of CSC from 2.6% to 0.4% (FIG. 12A). Overall results are represented as ratio between percent ALDH+ cells in treated conditions vs percent ALDH+ cells in DMSO. As previously described, compound 12 reduces the aldefluor ratio whereas treatment with doxorubicin increases it (FIG. 12B)

Example 13

Compounds that Induces Tumor Apoptosis in MMTV-ErB2/Neu Mice

DNA fragmentation in apoptotic cells was analyzed by the TUNEL assay (ApopTag detection kit, Millipore) as recommended by the manufacturer.

Briefly, 4 μm sections of paraffin-embedded fixed tissue from tumors derived from MMTC-ErbB2/neu mice treated with vehicle or with Compound 12, 4 or 8 (100 mg/kg) for 30 days, were deparaffined with successive histolemon and ethanol washes, then treated with 20 μg/mL proteinase K for 15 min at room temperature. Endogenous peroxidise was quenched with 3% hydrogen peroxide. Digoxigenin-dNTPs were enzymatically added to the free 3'OH DNA termini by terminal deoxynucleotidyl transferase (TdT) and revealed by the peroxidise anti-digoxygenin antibody. Coloration was performed using the diaminobenzidine mixed substrate (Dako). Counterstaining was done with a solution of 1% methyl green for 5 min at room temperature. After distilled water and N-butanol washes, specimens were mounted in Pertex medium (CellPath). Observations were made using the Leica DMD108 digital microimaging device (Leica Microsystems GmbH).

The inventors determined the percentage of cells having TdT positive nuclei in each condition. They observed that, while the percentage of TdT positive nuclei was rare in tumors from mice treated with vehicle or with Compound 8, it reached 50% in tumors from mice treated with Compound 4 and even 70% in tumors from mice treated with Compound 12.

The invention claimed is:

1. A compound of formula (I):

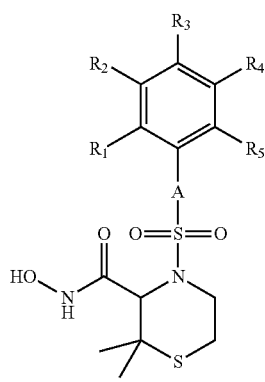

(I)

wherein $R_1$, $R_2$, $R_4$ and $R_5$ are independently selected from the group consisting of:
H,
optionally substituted, branched or linear $C_1$-$C_{12}$ alkyl,
optionally substituted, branched or linear $C_2$-$C_{12}$ alkenyl,
halogen atom,
$C_1$-$C_{12}$ haloalkyl,
$(CH_2)_a R^a$ wherein a is comprised from 1 to 12 and $R^a$ is selected from the group consisting of:

$OR^{a1}$, wherein $R^{a1}$ is selected from the group consisting of optionally substituted $C_1$-$C_{12}$ alkyl, optionally substituted $C_6$-$C_{10}$ aryl, optionally substituted $C_3$-$C_{12}$ cycloalkyl, optionally substituted $C_2$-$C_6$ heterocycloalkyl and optionally substituted $C_1$-$C_{10}$ heteroaryl, and $R^{a2}$ wherein $R^{a2}$ is selected from the group consisting of optionally substituted $C_6$-$C_{10}$ aryl, optionally substituted $C_3$-$C_{12}$ cycloalkyl, optionally substituted $C_2$-$C_6$ heterocycloalkyl and optionally substituted $C_1$-$C_{10}$ heteroaryl, $(CH_2)_b R^b$ wherein b is comprised from 0 to 12 and $R^b$ is selected from the group consisting of:
CN,
OH,
$C(O)R^{b1}$ and $SO_2 R^{b1}$, wherein $R^{b1}$ is selected from the group consisting of H, OH, optionally substituted $C_1$-$C_{12}$ alkyl, optionally substituted $C_6$-$C_{10}$ aryl, optionally substituted $C_3$-$C_{12}$ cycloalkyl, optionally substituted $C_2$-$C_6$ heterocycloalkyl and optionally substituted $C_1$-$C_{10}$ heteroaryl, and
$NHR^{b2}$ and $NHC(O)R^{b2}$ wherein $R^{b2}$ is selected from the group consisting of H, optionally substituted $C_1$-$C_{12}$ alkyl, wherein $R_3$ is selected from the group consisting of:
H,
optionally substituted, branched or linear $C_1$-$C_{12}$ alkyl,
optionally substituted, branched or linear $C_2$-$C_{12}$ alkenyl,
halogen atom,
$C_1$-$C_{12}$ haloalkyl,
$(CH_2)_a R^a$ wherein a is comprised from 1 to 12 and $R^a$ is selected from the group consisting of:

$OR^{a1}$, wherein $R^{a1}$ is selected from the group consisting of optionally substituted $C_1$-$C_{12}$ alkyl, optionally substituted $C_3$-$C_{12}$ cycloalkyl, and optionally substituted $C_2$-$C_6$ heterocycloalkyl, and $R^{a2}$ wherein $R^{a2}$ is selected from the group consisting of optionally substituted $C_6$-$C_{10}$ aryl, optionally substituted $C_3$-$C_{12}$ cycloalkyl, optionally substituted $C_2$-$C_6$ heterocycloalkyl and optionally substituted $C_1$-$C_{10}$ heteroaryl, $(CH_2)_b R^b$ wherein b and $R^b$ are as defined above, and wherein A represents a single bond or a $C_1$-$C_6$ alkylene radical, optionally substituted by a $C_1$-$C_6$ alkyl or a $C_6$-$C_{10}$ aryl group.

2. The compound according to claim 1, wherein $R_3$ is selected from the group consisting of:
H,
optionally substituted, branched or linear $C_1$-$C_{12}$ alkyl,
optionally substituted, branched or linear $C_2$-$C_{12}$ alkenyl,
halogen atom,
$C_1$-$C_{12}$ haloalkyl,
$(CH_2)_a R^a$ wherein a is comprised from 1 to 12 and $R^a$ is selected from the group consisting of optionally substituted $C_6$-$C_{10}$ aryl, optionally substituted $C_3$-$C_{12}$ cycloalkyl, optionally substituted $C_2$-$C_6$ heterocycloalkyl and optionally substituted $C_1$-$C_{10}$ heteroaryl, and
$(CH_2)_b R^b$ wherein b and $R^b$ are as defined in claim 1.

3. The compound according to claim 1, wherein $R_3$ is selected from the group consisting of:
H,
optionally substituted, branched or linear $C_1$-$C_{12}$ alkyl,
optionally substituted, branched or linear $C_2$-$C_{12}$ alkenyl,
halogen atom,
$C_1$-$C_{12}$ haloalkyl,
$(CH_2)_a R^a$ wherein a is comprised from 1 to 12 and $R^a$ is selected from the group consisting of optionally substituted $C_3$-$C_{12}$ cycloalkyl, and optionally substituted $C_2$-$C_6$ heterocycloalkyl, and
$(CH_2)_b R^b$ wherein b and $R^b$ are as defined in claim 1.

4. The compound according to claim 1, wherein $R_1, R_2, R_3, R_4$ and $R_5$ are independently selected from the group consisting of:
H,
optionally substituted, branched or linear $C_1$-$C_{12}$ alkyl,
halogen atom, and
$C_1$-$C_{12}$ haloalkyl.

5. The compound according to claim 1 of formula (II):

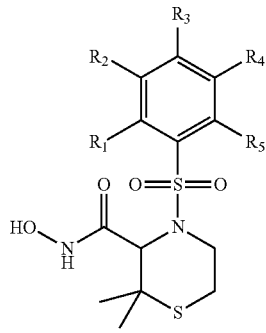

(II)

wherein $R_1, R_2, R_3, R_4$ and $R_5$ are defined as in claim 1.

6. The compound according to claim 1 of formula (II-1):

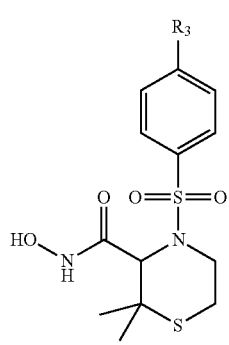

(II-1)

wherein $R_3$ is defined as in claim 1.

7. The compound according to claim 1, wherein $R_3$ is selected from the group consisting of: H, methyl, ethyl, propyl, isopropyl, dodecyl, bromomethyl, trifluoromethyl and fluor.

8. The compound according to claim 1 of formula (II-2):

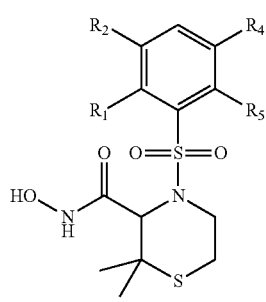

(II-2)

wherein $R_1, R_2, R_4$ and $R_5$ are defined as in claim 1.

9. The compound according to claim 8, wherein $R_1, R_2, R_4$ and $R_5$ are independently selected from the group consisting of: H and methyl.

10. The compound according to claim 1 of formula (II-3):

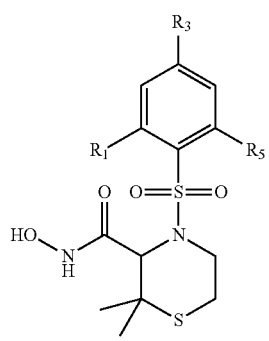

(II-3)

wherein $R_1, R_3$ and $R_5$ are defined as in claim 1.

11. The compound according to claim 10, wherein $R_1, R_3$ and $R_5$ are independently selected from the group consisting of: H, methyl and isopropyl.

12. The compound according to claim 1, wherein $R_1$=$R_5$.

13. The compound according to claim 1, wherein $R_2$=$R_4$.

14. The compound according to claim 1, selected from the following compounds:

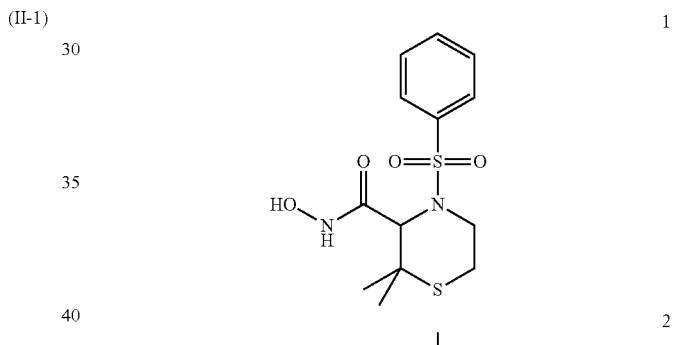

1

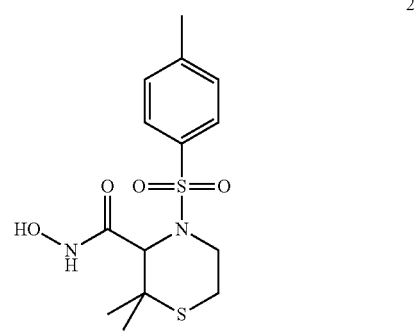

2

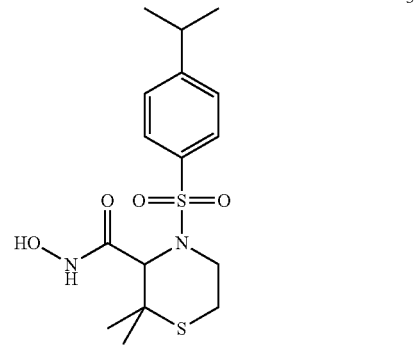

3

| 4 | 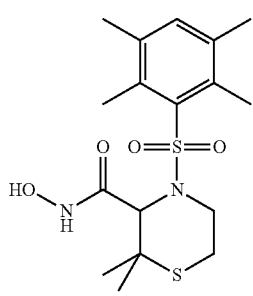 | 8 | 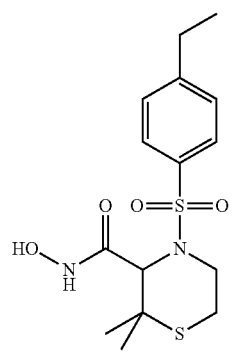 |
|---|---|---|---|
| 5 | 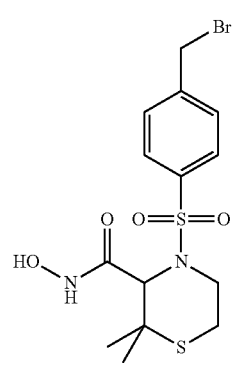 | 9 | 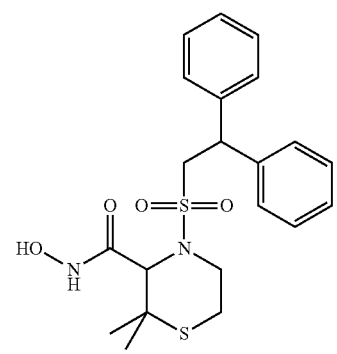 |
| 6 | 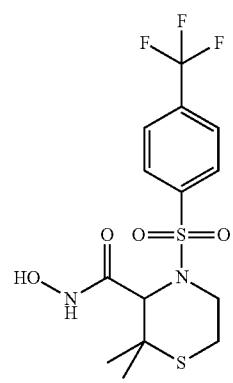 | 10 | 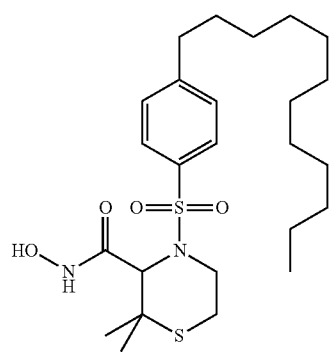 |
| 7 | 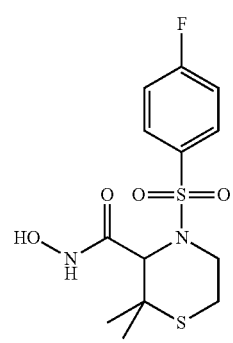 | 11 | 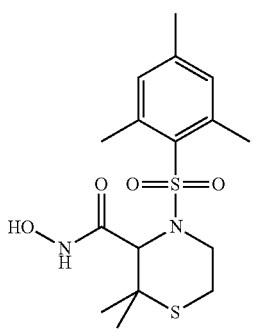 |

-continued

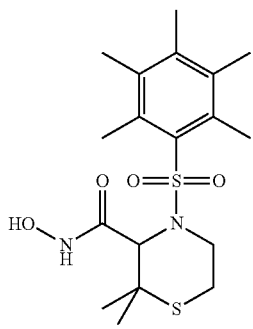

12

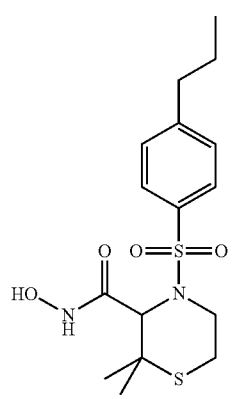

13

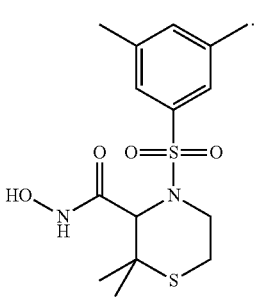

14

15. A pharmaceutical composition comprising the compound according to claim 1 and a pharmaceutically acceptable carrier.

16. A method of preparation of the compound according to claim 1, comprising a step of coupling 2,2-dimethyl-3-thiomorpholic acid and a compound of formula (III):

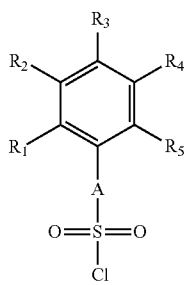

(III)

providing a compound of formula (IV):

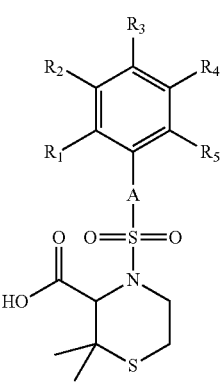

(IV)

wherein A, $R_1$, $R_2$, $R_3$, $R_4$ and $R_5$ are defined as in claim 1.

17. A method for the treatment of human cancers selected from the group consisting of breast cancer, pancreas cancer, prostate cancer, bone cancer, liver cancer, lung cancer, ovary cancer, uterus cancer, kidney cancer, brain cancer, skin cancer, colon cancer, blood cancer, stomach cancer, thyroid cancer, and mouth cancer in a patient in need thereof, comprising administering to said patient a therapeutically effective amount of the compound according to claim 1.

* * * * *